US010288590B2

(12) United States Patent
Hammond et al.

(10) Patent No.: US 10,288,590 B2
(45) Date of Patent: *May 14, 2019

(54) PH INDICATOR DEVICE AND FORMULATION

(71) Applicant: Smith & Nephew PLC, London (GB)

(72) Inventors: Victoria Jody Hammond, Hull (GB); John Kenneth Hicks, Pocklington (GB)

(73) Assignee: Smith & Nephew PLC, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/804,748

(22) Filed: Nov. 6, 2017

(65) Prior Publication Data

US 2018/0196021 A1 Jul. 12, 2018

Related U.S. Application Data

(63) Continuation of application No. 14/650,547, filed as application No. PCT/EP2014/071520 on Oct. 8, 2014, now Pat. No. 9,829,471.

(30) Foreign Application Priority Data

Oct. 8, 2013 (GB) .................................... 1317746.4

(51) Int. Cl.
*G01N 31/22* (2006.01)
*G01N 27/416* (2006.01)
(Continued)

(52) U.S. Cl.
CPC ........ *G01N 31/221* (2013.01); *A61B 5/14539* (2013.01); *A61F 2013/427* (2013.01); *G01N 21/80* (2013.01); *G01N 27/4165* (2013.01)

(58) Field of Classification Search
CPC ........ A61B 5/14539; A61B 2562/0295; A61B 5/1032; A61B 5/6802; A61F 2013/427;
(Continued)

(56) References Cited

U.S. PATENT DOCUMENTS 2,249,867 A 7/1941 Snelling
3,675,654 A 7/1972 Baker et al.
(Continued)

FOREIGN PATENT DOCUMENTS

AU 2003204827 5/2006
CN 101490556 7/2009
(Continued)

OTHER PUBLICATIONS

International Search Report, re PCT Application No. PCT/EP2014/071510, dated Feb. 5, 2015.
(Continued)

*Primary Examiner* — Lyle Alexander
*Assistant Examiner* — Bryan Kilpatrick
(74) *Attorney, Agent, or Firm* — Knobbe, Martens, Olson & Bear, LLP

(57) ABSTRACT

Disclosed herein are devices and methods for determining the pH of fluid. Example devices include a device comprising a surface configured to contact the fluid and a pH indicator covalently bound thereto, wherein the pH indicator has a first color prior to contact with the fluid and changes color as a function of the pH of the fluid.

17 Claims, 25 Drawing Sheets

(51) Int. Cl.
*G01N 21/80* (2006.01)
*A61B 5/145* (2006.01)
*A61F 13/42* (2006.01)

(58) Field of Classification Search
CPC ............ A61F 13/00063; A61F 13/0206; A61F 2013/00153; G01N 21/80; G01N 27/4165; G01N 31/221; G01N 21/78; A61M 2230/208
See application file for complete search history.

(56) References Cited

U.S. PATENT DOCUMENTS

| | | | |
|---|---|---|---|
| 3,759,261 A | 9/1973 | Wang | |
| 3,896,802 A | 7/1975 | Williams | |
| 3,972,328 A | 8/1976 | Chen | |
| 4,029,598 A | 6/1977 | Neisius et al. | |
| 4,192,311 A | 3/1980 | Felfoldi | |
| 4,705,513 A | 11/1987 | Sheldon et al. | |
| 4,728,499 A | 3/1988 | Fehder | |
| 4,813,942 A | 3/1989 | Alvarez | |
| 4,885,077 A | 12/1989 | Karakelle et al. | |
| 4,999,306 A | 3/1991 | Yafuso et al. | |
| 5,056,510 A | 10/1991 | Gilman | |
| 5,104,660 A | 4/1992 | Chvapil et al. | |
| 5,181,905 A | 1/1993 | Flam | |
| 5,238,732 A | 8/1993 | Krishnan | |
| 5,277,872 A | 1/1994 | Bankert et al. | |
| 5,536,783 A | 7/1996 | Olstein et al. | |
| 5,549,584 A | 8/1996 | Gross | |
| 5,571,684 A | 11/1996 | Lawrence et al. | |
| 5,678,448 A | 10/1997 | Fullen et al. | |
| 5,690,610 A | 11/1997 | Ito et al. | |
| 5,690,624 A | 11/1997 | Sasaki et al. | |
| 5,707,499 A | 1/1998 | Joshi et al. | |
| 5,759,570 A | 6/1998 | Arnold | |
| 5,766,212 A | 6/1998 | Jitoe et al. | |
| 5,788,687 A | 8/1998 | Batich et al. | |
| 5,852,126 A | 12/1998 | Barnard et al. | |
| 5,853,669 A | 12/1998 | Wolfbeis | |
| 5,897,516 A | 4/1999 | Kadash et al. | |
| 6,071,267 A | 6/2000 | Zamierowski | |
| 6,095,992 A | 8/2000 | Augustine | |
| 6,120,904 A | 9/2000 | Hostettler et al. | |
| 6,284,942 B1 | 9/2001 | Rabin | |
| 6,333,093 B1 | 12/2001 | Burrell et al. | |
| 6,381,482 B1 | 4/2002 | Jayaraman et al. | |
| 6,388,043 B1 | 5/2002 | Langer et al. | |
| 6,482,491 B1 | 11/2002 | Samuelsen et al. | |
| 6,517,484 B1 | 2/2003 | Wilk et al. | |
| 6,551,252 B2 | 4/2003 | Sackner et al. | |
| 6,626,891 B2 | 9/2003 | Ohmstede | |
| 6,685,681 B2 | 2/2004 | Lockwood et al. | |
| 6,688,525 B1 | 2/2004 | Nelson et al. | |
| 6,696,240 B1 | 2/2004 | Kloepfer et al. | |
| 6,731,987 B1 | 5/2004 | McAdams et al. | |
| 6,747,185 B2 | 6/2004 | Inoue et al. | |
| 6,752,794 B2 | 6/2004 | Lockwood et al. | |
| 6,772,708 B2 | 8/2004 | Klofta et al. | |
| 6,936,037 B2 | 8/2005 | Bubb et al. | |
| 6,951,553 B2 | 10/2005 | Bubb et al. | |
| 6,979,324 B2 | 12/2005 | Bybordi et al. | |
| 7,004,915 B2 | 2/2006 | Boynton et al. | |
| 7,070,584 B2 | 7/2006 | Johnson et al. | |
| 7,077,832 B2 | 7/2006 | Fleischmann | |
| 7,108,683 B2 | 9/2006 | Zamierowski | |
| 7,159,532 B2 | 1/2007 | Klofta et al. | |
| 7,201,063 B2 | 4/2007 | Taylor et al. | |
| 7,206,623 B2 | 4/2007 | Blank et al. | |
| 7,216,651 B2 | 5/2007 | Argenta et al. | |
| 7,316,652 B2 | 1/2008 | Dalgaard et al. | |
| 7,361,184 B2 | 4/2008 | Joshi | |
| 7,381,859 B2 | 6/2008 | Hunt et al. | |
| 7,429,255 B2 | 9/2008 | Thompson | |
| 7,520,875 B2 | 4/2009 | Bernabei | |
| 7,521,292 B2 | 4/2009 | Rogers et al. | |
| 7,569,742 B2 | 8/2009 | Haggstrom et al. | |
| 7,605,298 B2 | 10/2009 | Bechert et al. | |
| 7,615,036 B2 | 11/2009 | Joshi et al. | |
| 7,622,629 B2 | 11/2009 | Aail | |
| 7,625,362 B2 | 12/2009 | Boehringer et al. | |
| 7,687,678 B2 | 3/2010 | Jacobs | |
| 7,699,823 B2 | 4/2010 | Haggstrom et al. | |
| 7,708,724 B2 | 5/2010 | Weston | |
| 7,722,582 B2 | 5/2010 | Lina et al. | |
| 7,749,531 B2 | 7/2010 | Booher | |
| 7,759,537 B2 | 7/2010 | Bishop et al. | |
| 7,759,539 B2 | 7/2010 | Shaw et al. | |
| 7,775,998 B2 | 8/2010 | Riesinger | |
| 7,777,092 B2 | 8/2010 | Lykke et al. | |
| 7,779,625 B2 | 8/2010 | Joshi et al. | |
| 7,811,269 B2 | 10/2010 | Boynton et al. | |
| 7,838,717 B2 | 11/2010 | Haggstrom et al. | |
| 7,846,141 B2 | 12/2010 | Weston | |
| 7,873,141 B2 | 1/2011 | Imai et al. | |
| 7,877,866 B1 | 2/2011 | Greenberg et al. | |
| 7,904,133 B2 | 3/2011 | Gehman et al. | |
| 7,910,791 B2 | 3/2011 | Coffey | |
| 7,922,703 B2 | 4/2011 | Riesinger | |
| 7,945,302 B2 | 5/2011 | McAdams | |
| 7,959,624 B2 | 6/2011 | Riesinger | |
| 7,964,766 B2 | 6/2011 | Blott et al. | |
| 7,976,519 B2 | 7/2011 | Bubb et al. | |
| 8,019,401 B1 | 9/2011 | Smith et al. | |
| 8,032,210 B2 | 10/2011 | Finneran et al. | |
| 8,034,037 B2 | 10/2011 | Adams et al. | |
| 8,060,174 B2 | 11/2011 | Simpson et al. | |
| 8,062,272 B2 | 11/2011 | Weston | |
| 8,062,331 B2 | 11/2011 | Zamierowski | |
| 8,079,247 B2 | 12/2011 | Russell et al. | |
| 8,080,702 B2 | 12/2011 | Blott et al. | |
| 8,111,165 B2 | 2/2012 | Ortega et al. | |
| 8,116,841 B2 | 2/2012 | Bly et al. | |
| 8,118,794 B2 | 2/2012 | Weston et al. | |
| 8,152,785 B2 | 4/2012 | Vitaris | |
| 8,162,907 B2 | 4/2012 | Heagle | |
| 8,207,392 B2 | 6/2012 | Haggstrom et al. | |
| 8,238,996 B2 | 8/2012 | Burnes | |
| 8,241,231 B2 | 8/2012 | Bausewein et al. | |
| 8,241,261 B2 | 8/2012 | Randolph et al. | |
| 8,282,611 B2 | 10/2012 | Weston | |
| 8,303,552 B2 | 11/2012 | Weston | |
| 8,332,053 B1 | 12/2012 | Patterson et al. | |
| 8,333,874 B2 | 12/2012 | Currie et al. | |
| 8,366,692 B2 | 2/2013 | Weston | |
| 8,372,049 B2 | 2/2013 | Jaeb et al. | |
| 8,372,050 B2 | 2/2013 | Jaeb et al. | |
| 8,425,478 B2 | 4/2013 | Olson | |
| 8,425,996 B2 | 4/2013 | Gorski et al. | |
| 8,444,612 B2 | 5/2013 | Patel et al. | |
| 8,460,255 B2 | 6/2013 | Joshi et al. | |
| 8,480,641 B2 | 7/2013 | Jacobs | |
| 8,545,466 B2 | 10/2013 | Andresen et al. | |
| 8,568,386 B2 | 10/2013 | Malhi | |
| 8,628,505 B2 | 1/2014 | Weston | |
| 8,641,691 B2 | 2/2014 | Fink | |
| 8,663,106 B2 | 3/2014 | Stivoric et al. | |
| 8,663,198 B2 | 3/2014 | Buan et al. | |
| 8,682,442 B2 | 3/2014 | McAdams | |
| 8,715,256 B2 | 5/2014 | Greener | |
| 8,764,732 B2 | 7/2014 | Hartwell | |
| 8,783,948 B2 | 7/2014 | Panda et al. | |
| 8,788,009 B2 | 7/2014 | Greene et al. | |
| 8,795,243 B2 | 8/2014 | Weston | |
| 8,795,257 B2 | 8/2014 | Coulthard et al. | |
| 8,800,386 B2 | 8/2014 | Taylor | |
| 8,808,274 B2 | 8/2014 | Hartwell | |
| 8,818,478 B2 | 8/2014 | Scheffler et al. | |
| 8,829,263 B2 | 9/2014 | Haggstrom et al. | |
| 8,834,451 B2 | 9/2014 | Blott et al. | |
| 8,894,590 B2 | 11/2014 | Lamoise et al. | |
| 8,925,392 B2 | 1/2015 | Esposito et al. | |
| 8,927,801 B2 | 1/2015 | Klofta | |
| 8,934,957 B2 | 1/2015 | Dias et al. | |

(56) References Cited

U.S. PATENT DOCUMENTS

| | | |
|---|---|---|
| 8,934,965 B2 | 1/2015 | Rogers et al. |
| 8,943,897 B2 | 2/2015 | Beauvais et al. |
| 8,948,839 B1 | 2/2015 | Longinotti-Buitoni et al. |
| 8,956,336 B2 | 2/2015 | Haggstrom et al. |
| 8,974,428 B2 | 3/2015 | Shuler et al. |
| 8,986,940 B2 | 3/2015 | McNulty et al. |
| 8,997,588 B2 | 4/2015 | Taylor |
| 9,000,251 B2 | 4/2015 | Murphy et al. |
| 9,012,714 B2 | 4/2015 | Fleischmann |
| 9,061,095 B2 | 6/2015 | Adie et al. |
| 9,127,665 B2 | 9/2015 | Locke et al. |
| 9,192,531 B2 | 11/2015 | Wu |
| 9,199,012 B2 | 12/2015 | Vitaris et al. |
| 9,204,806 B2 | 12/2015 | Stivoric et al. |
| 9,220,455 B2 | 12/2015 | Sarrafzadeh et al. |
| 9,220,822 B2 | 12/2015 | Hartwell et al. |
| 9,226,402 B2 | 12/2015 | Hsu |
| 9,282,897 B2 | 3/2016 | Ross, Jr. et al. |
| 9,283,118 B2 | 3/2016 | Locke et al. |
| 9,302,033 B2 | 4/2016 | Riesinger |
| 9,311,520 B2 | 4/2016 | Burg et al. |
| 9,314,175 B2 | 4/2016 | Jacofsky et al. |
| 9,320,473 B2 | 4/2016 | Shuler |
| 9,372,123 B2 | 6/2016 | Li et al. |
| 9,375,353 B2 | 6/2016 | Vitaris et al. |
| 9,375,521 B2 | 6/2016 | Hudspeth et al. |
| 9,381,283 B2 | 7/2016 | Adams et al. |
| 9,402,988 B2 | 8/2016 | Buchanan et al. |
| 9,408,573 B2 | 8/2016 | Welch et al. |
| 9,421,309 B2 | 8/2016 | Robinson et al. |
| 9,427,179 B2 | 8/2016 | Mestrovic et al. |
| 9,439,599 B2 | 9/2016 | Thompson et al. |
| 9,445,749 B2 | 9/2016 | Erickson et al. |
| 9,446,178 B2 | 9/2016 | Blott et al. |
| 9,494,474 B2 | 11/2016 | Servati et al. |
| 9,511,215 B2 | 12/2016 | Skiba |
| 9,516,758 B2 | 12/2016 | Arora et al. |
| 9,526,439 B2 | 12/2016 | Connelly et al. |
| 9,554,484 B2 | 1/2017 | Rogers et al. |
| 9,572,507 B2 | 2/2017 | Moore et al. |
| 9,582,072 B2 | 2/2017 | Connor |
| 9,585,620 B2 | 3/2017 | Paquet et al. |
| 9,587,991 B2 | 3/2017 | Padiy |
| 9,592,007 B2 | 3/2017 | Nuovo et al. |
| 9,603,560 B2 | 3/2017 | Monty et al. |
| 9,613,911 B2 | 4/2017 | Rogers et al. |
| 9,629,584 B2 | 4/2017 | Macia Barber et al. |
| 9,629,986 B2 | 4/2017 | Patel et al. |
| 9,681,993 B2 | 6/2017 | Wu et al. |
| 9,687,195 B2 | 6/2017 | Sims et al. |
| 9,829,471 B2 * | 11/2017 | Hammond ............ G01N 31/221 |
| 10,004,643 B2 | 6/2018 | Luckemeyer et al. |
| 2002/0062114 A1 | 5/2002 | Murai et al. |
| 2002/0091347 A1 | 7/2002 | Eakin |
| 2003/0033032 A1 | 2/2003 | Lind et al. |
| 2003/0210810 A1 | 11/2003 | Gee, Jr. et al. |
| 2004/0044299 A1 | 3/2004 | Utsugi |
| 2004/0133090 A1 | 7/2004 | Dostoinov et al. |
| 2004/0230132 A1 | 11/2004 | Shehada |
| 2005/0105789 A1 | 5/2005 | Isaacs et al. |
| 2005/0187146 A1 | 8/2005 | Helmus et al. |
| 2005/0199055 A1 | 9/2005 | Browne |
| 2005/0280531 A1 | 12/2005 | Fadem et al. |
| 2006/0009744 A1 | 1/2006 | Erdman et al. |
| 2006/0140999 A1 | 6/2006 | Lendlein et al. |
| 2007/0048224 A1 | 3/2007 | Howell et al. |
| 2007/0055209 A1 | 3/2007 | Patel et al. |
| 2007/0129784 A1 | 6/2007 | Lendlein et al. |
| 2007/0142762 A1 | 6/2007 | Kaplan et al. |
| 2007/0173892 A1 | 7/2007 | Fleischer et al. |
| 2007/0188759 A1 | 8/2007 | Mehendale et al. |
| 2007/0191754 A1 | 8/2007 | Aali |
| 2007/0225663 A1 | 9/2007 | Watt et al. |
| 2007/0270774 A1 | 11/2007 | Bergman et al. |
| 2007/0276207 A1 | 11/2007 | Eagland et al. |
| 2008/0132821 A1 | 6/2008 | Propp et al. |
| 2008/0167535 A1 | 7/2008 | Stivoric et al. |
| 2008/0208151 A1 | 8/2008 | Zacharias et al. |
| 2008/0306456 A1 | 12/2008 | Riesinger |
| 2008/0319283 A1 | 12/2008 | Cotton et al. |
| 2009/0062757 A1 | 3/2009 | Long et al. |
| 2009/0125004 A1 | 5/2009 | Shen et al. |
| 2009/0157024 A1 | 6/2009 | Song |
| 2009/0190135 A1 | 7/2009 | Clarizia et al. |
| 2009/0234306 A1 | 9/2009 | Vitaris |
| 2009/0245601 A1 | 10/2009 | Cohen et al. |
| 2009/0299251 A1 | 12/2009 | Buan |
| 2009/0299306 A1 | 12/2009 | Buan |
| 2010/0022990 A1 | 1/2010 | Karpowicz et al. |
| 2010/0025831 A1 | 2/2010 | Yamazaki et al. |
| 2010/0041968 A1 | 2/2010 | Meschisen et al. |
| 2010/0112680 A1 | 5/2010 | Brockwell et al. |
| 2010/0125258 A1 | 5/2010 | Coulthard et al. |
| 2010/0166252 A1 | 7/2010 | Ahmed et al. |
| 2010/0168695 A1 | 7/2010 | Robles et al. |
| 2010/0168700 A1 | 7/2010 | Schmidt et al. |
| 2010/0168727 A1 | 7/2010 | Hancock et al. |
| 2010/0178203 A1 | 7/2010 | Kane et al. |
| 2010/0268111 A1 | 10/2010 | Drinan et al. |
| 2010/0305473 A1 | 12/2010 | Yuzhakov |
| 2010/0318052 A1 | 12/2010 | Ha et al. |
| 2011/0004088 A1 | 1/2011 | Grossman |
| 2011/0004172 A1 | 1/2011 | Eckstein et al. |
| 2011/0054283 A1 | 3/2011 | Shuler |
| 2011/0092958 A1 | 4/2011 | Jacobs |
| 2011/0118683 A1 | 5/2011 | Weston |
| 2011/0218757 A1 | 9/2011 | Callsen et al. |
| 2011/0224631 A1 | 9/2011 | Simmons |
| 2011/0245682 A1 | 10/2011 | Robinson et al. |
| 2011/0274593 A1 | 11/2011 | Gorski et al. |
| 2011/0301441 A1 | 12/2011 | Bandic et al. |
| 2012/0029306 A1 | 2/2012 | Paquet et al. |
| 2012/0029307 A1 | 2/2012 | Paquet et al. |
| 2012/0029410 A1 | 2/2012 | Koenig et al. |
| 2012/0095380 A1 | 4/2012 | Gergley et al. |
| 2012/0165717 A1 | 6/2012 | Al Khaburi et al. |
| 2012/0190956 A1 | 7/2012 | Connolly |
| 2012/0190989 A1 | 7/2012 | Kaiser et al. |
| 2012/0201437 A1 | 8/2012 | Ohnemus |
| 2012/0215190 A1 | 8/2012 | Kawashima |
| 2012/0256750 A1 | 10/2012 | Novak |
| 2012/0264163 A1 | 10/2012 | Booher |
| 2012/0271265 A1 | 10/2012 | Langdon |
| 2012/0277559 A1 | 11/2012 | Kohl-Bareis et al. |
| 2012/0279101 A1 | 11/2012 | Pretsch et al. |
| 2012/0316538 A1 | 12/2012 | Heiser et al. |
| 2012/0323274 A1 | 12/2012 | Lendlein et al. |
| 2013/0041235 A1 | 2/2013 | Rogers et al. |
| 2013/0064772 A1 | 3/2013 | Swiss et al. |
| 2013/0066285 A1 | 3/2013 | Locke et al. |
| 2013/0066289 A1 | 3/2013 | Song et al. |
| 2013/0087298 A1 | 4/2013 | Phillips et al. |
| 2013/0090616 A1 | 4/2013 | Neubauer |
| 2013/0121544 A1 | 5/2013 | Sarrafzadeh et al. |
| 2013/0131621 A1 | 5/2013 | Van Holten et al. |
| 2013/0138054 A1 | 5/2013 | Fleischmann |
| 2013/0150814 A1 | 6/2013 | Buan |
| 2013/0151223 A1 | 6/2013 | Zamierowski et al. |
| 2013/0165878 A1 | 6/2013 | Heagle |
| 2013/0200268 A1 | 8/2013 | Rafferty et al. |
| 2013/0261409 A1 | 10/2013 | Pathak et al. |
| 2013/0274629 A1 | 10/2013 | Duesterhoft et al. |
| 2013/0274688 A1 | 10/2013 | Weston |
| 2013/0303865 A1 | 11/2013 | Rebec et al. |
| 2013/0317367 A1 | 11/2013 | Shuler |
| 2014/0031663 A1 | 1/2014 | Gallego et al. |
| 2014/0072190 A1 | 3/2014 | Wu et al. |
| 2014/0098209 A1 | 4/2014 | Neff |
| 2014/0107495 A1 | 4/2014 | Marinelli et al. |
| 2014/0114268 A1 | 4/2014 | Auguste et al. |
| 2014/0121487 A1 | 5/2014 | Faybishenko et al. |
| 2014/0138441 A1 | 5/2014 | Davalos et al. |
| 2014/0147611 A1 | 5/2014 | Ackerman, Jr. et al. |
| 2014/0154789 A1 | 6/2014 | Polwart et al. |

(56) References Cited

U.S. PATENT DOCUMENTS

| | | | |
|---|---|---|---|
| 2014/0203797 A1 | 7/2014 | Stivoric et al. |
| 2014/0206947 A1 | 7/2014 | Isserow et al. |
| 2014/0228791 A1 | 8/2014 | Hartwell |
| 2014/0232516 A1 | 8/2014 | Stivoric et al. |
| 2014/0243709 A1 | 8/2014 | Gibson et al. |
| 2014/0296749 A1 | 10/2014 | Reid, Jr. et al. |
| 2014/0296808 A1 | 10/2014 | Curran et al. |
| 2014/0298927 A1 | 10/2014 | Allin et al. |
| 2014/0316359 A1 | 10/2014 | Collinson et al. |
| 2014/0340857 A1 | 11/2014 | Hsu et al. |
| 2014/0350882 A1 | 11/2014 | Everett et al. |
| 2015/0025343 A1 | 1/2015 | Gareau et al. |
| 2015/0032035 A1 | 1/2015 | Banwell et al. |
| 2015/0055134 A1 | 2/2015 | Papautsky et al. |
| 2015/0065965 A1 | 3/2015 | Haggstrom et al. |
| 2015/0080685 A1 | 3/2015 | Markle et al. |
| 2015/0138330 A1 | 5/2015 | Krishnamoorthi |
| 2015/0141767 A1 | 5/2015 | Rogers et al. |
| 2015/0182166 A1 | 7/2015 | Evans et al. |
| 2015/0223716 A1 | 8/2015 | Korkala et al. |
| 2015/0257644 A1 | 9/2015 | Cao |
| 2015/0265743 A1 | 9/2015 | Hanson et al. |
| 2015/0292968 A1 | 10/2015 | Vogt et al. |
| 2015/0313476 A1 | 11/2015 | Pisani et al. |
| 2015/0313533 A1 | 11/2015 | Rapp et al. |
| 2015/0327777 A1 | 11/2015 | Kostic et al. |
| 2015/0335254 A1 | 11/2015 | Fastert et al. |
| 2015/0335288 A1 | 11/2015 | Toth et al. |
| 2015/0351970 A1 | 12/2015 | Dagger et al. |
| 2015/0359485 A1 | 12/2015 | Berg et al. |
| 2016/0015962 A1 | 1/2016 | Shokoueinejad Maragheh |
| 2016/0022223 A1 | 1/2016 | Grundfest et al. |
| 2016/0029900 A1 | 2/2016 | LaPlante et al. |
| 2016/0038064 A1 | 2/2016 | Johnson |
| 2016/0038083 A1 | 2/2016 | Ding et al. |
| 2016/0058380 A1 | 3/2016 | Lee et al. |
| 2016/0066854 A1 | 3/2016 | Mei et al. |
| 2016/0069743 A1 | 3/2016 | McQuilkin et al. |
| 2016/0074234 A1 | 3/2016 | Abichandi et al. |
| 2016/0081580 A1 | 3/2016 | Bergelin et al. |
| 2016/0100790 A1 | 4/2016 | Cantu et al. |
| 2016/0100987 A1 | 4/2016 | Hartwell et al. |
| 2016/0101282 A1 | 4/2016 | Bergelin et al. |
| 2016/0144084 A1 | 5/2016 | Collinson et al. |
| 2016/0232807 A1 | 8/2016 | Ghaffari et al. |
| 2016/0249810 A1 | 9/2016 | Darty et al. |
| 2016/0262672 A1 | 9/2016 | Hammond et al. |
| 2016/0262687 A1 | 9/2016 | Vaidyanathan et al. |
| 2016/0287177 A1 | 10/2016 | Huppert et al. |
| 2016/0298620 A1 | 10/2016 | Cordoba et al. |
| 2016/0302729 A1 | 10/2016 | Starr et al. |
| 2016/0354001 A1 | 12/2016 | Buckley et al. |
| 2016/0367189 A1 | 12/2016 | Aimone et al. |
| 2016/0367406 A1 | 12/2016 | Barnett |
| 2017/0000407 A1 | 1/2017 | Saxby et al. |
| 2017/0027498 A1 | 2/2017 | Larson et al. |
| 2017/0079740 A1 | 3/2017 | Hufnagel et al. |
| 2017/0086519 A1 | 3/2017 | Vigano et al. |
| 2017/0086709 A1 | 3/2017 | Khine et al. |
| 2017/0095208 A1 | 4/2017 | Oberleitner et al. |
| 2017/0161893 A1 | 6/2017 | Carnes et al. |
| 2017/0164865 A1 | 6/2017 | Rafferty et al. |
| 2017/0164876 A1 | 6/2017 | Hyde et al. |
| 2017/0172439 A1 | 6/2017 | Zhu et al. |
| 2017/0183705 A1 | 6/2017 | Hicks et al. |
| 2017/0234802 A1 | 8/2017 | Hicks et al. |
| 2018/0008177 A1 | 1/2018 | Shimuta et al. |

FOREIGN PATENT DOCUMENTS

| | | |
|---|---|---|
| CN | 201414880 | 3/2010 |
| CN | 103217503 | 7/2013 |
| CN | 105395184 | 3/2016 |
| DE | 34 43 101 | 5/1986 |
| DE | 20 2004 017 052 | 7/2005 |
| EP | 0 257 916 | 3/1988 |
| EP | 0 340 018 | 11/1989 |
| EP | 0 430 608 | 6/1991 |
| EP | 1 476 217 | 3/2008 |
| EP | 2 021 046 | 3/2012 |
| EP | 2 454 990 | 5/2012 |
| EP | 2 462 908 | 6/2012 |
| EP | 2 574 275 | 4/2013 |
| EP | 1 854 342 | 6/2014 |
| EP | 1 734 858 | 7/2014 |
| EP | 2 544 642 | 1/2015 |
| EP | 2 648 668 | 1/2015 |
| EP | 2 451 349 | 4/2016 |
| EP | 2 941 195 | 12/2016 |
| FR | 1 163 907 | 10/1958 |
| GB | 905040 | 9/1962 |
| GB | 1255395 | 12/1971 |
| JP | S54-176283 | 12/1979 |
| JP | S57-162304 | 10/1982 |
| JP | H07-055788 | 3/1995 |
| JP | 2002-165757 | 6/2002 |
| JP | 2006-338521 | 12/2006 |
| JP | 2007-163350 | 6/2007 |
| JP | 2012-157438 | 8/2012 |
| KR | 20120059006 | 6/2012 |
| RU | 114854 | 4/2012 |
| WO | WO 1983/00742 | 3/1983 |
| WO | WO 1995/029959 | 11/1995 |
| WO | WO 1996/05873 | 2/1996 |
| WO | WO 1998/12996 | 4/1998 |
| WO | WO 1999/12581 | 3/1999 |
| WO | WO 2002/047737 | 6/2002 |
| WO | WO 2005/025447 | 3/2005 |
| WO | WO 2005/052572 | 6/2005 |
| WO | WO 2005/123170 | 12/2005 |
| WO | WO 2006/052839 | 5/2006 |
| WO | WO 2006/110502 | 10/2006 |
| WO | WO 2006/133430 | 12/2006 |
| WO | WO 2007/030379 | 3/2007 |
| WO | WO 2008/003920 | 1/2008 |
| WO | WO 2008/006150 | 1/2008 |
| WO | WO 2008/010604 | 1/2008 |
| WO | WO 2008/125995 | 10/2008 |
| WO | WO 2009/066105 | 5/2009 |
| WO | WO 2009/124100 | 10/2009 |
| WO | WO 2009/141777 | 11/2009 |
| WO | WO 2009/158128 | 12/2009 |
| WO | WO 2010/020919 | 2/2010 |
| WO | WO 2010/105053 | 9/2010 |
| WO | WO 2010/142959 | 12/2010 |
| WO | WO 2011/098575 | 8/2011 |
| WO | WO 2011/135285 | 11/2011 |
| WO | WO 2011/135286 | 11/2011 |
| WO | WO 2011/135287 | 11/2011 |
| WO | WO 2011/144888 | 11/2011 |
| WO | WO 2012/074509 | 6/2012 |
| WO | WO 2012/131237 | 10/2012 |
| WO | WO 2012/131386 | 10/2012 |
| WO | WO 2012/140378 | 10/2012 |
| WO | WO 2012/143665 | 10/2012 |
| WO | WO 2013/010907 | 1/2013 |
| WO | WO 2013/026999 | 2/2013 |
| WO | WO 2013/044226 | 3/2013 |
| WO | WO 2013/074509 | 5/2013 |
| WO | WO 2013/083800 | 6/2013 |
| WO | WO 2013/090810 | 6/2013 |
| WO | WO 2013/136181 | 9/2013 |
| WO | WO 2013/149078 | 10/2013 |
| WO | WO 2014/008348 | 1/2014 |
| WO | WO 2014/016759 | 1/2014 |
| WO | WO 2014/020440 | 2/2014 |
| WO | WO 2014/020443 | 2/2014 |
| WO | WO 2014/066913 | 5/2014 |
| WO | WO 2014/108476 | 7/2014 |
| WO | WO 2014/113253 | 7/2014 |
| WO | WO 2014/113770 | 7/2014 |
| WO | WO 2015/022334 | 2/2015 |
| WO | WO 2015/022340 | 2/2015 |
| WO | WO 2015/031216 | 3/2015 |

(56) References Cited

FOREIGN PATENT DOCUMENTS

| WO | WO 2015/052225 | 4/2015 |
|---|---|---|
| WO | WO 2015/112095 | 7/2015 |
| WO | WO 2015/168720 | 11/2015 |
| WO | WO 2016/005288 | 1/2016 |
| WO | WO 2016/012219 | 1/2016 |
| WO | WO 2016/025438 | 2/2016 |
| WO | WO 2016/030752 | 3/2016 |

OTHER PUBLICATIONS

International Preliminary Report for Patentability, re PCT Application No. PCT/EP2014/071510, dated Apr. 21, 2016.
International Search Report and Written Opinion, re PCT Application No. PCT/EP2014/071520, dated Feb. 5, 2015.
International Preliminary Report for Patentability, re PCT Application No. PCT/EP2014/071520, dated Apr. 21, 2016.
Kendall ULTEC Hydrocolloid Dressing (4"×4"), product ordering page, web page downloaded Jul. 13, 2014.
Loh, B.Y. et al., "Automated Mobile pH Reader on a Camera Phone", IAENG International Journal of Computer Science, vol. 38(3), Aug. 2011, in 7 pages.
Advantec MFS, Inc., "Membrane Filters" (catalog), accessed Jan. 29, 2016 (publication date unknown, but believed to be copyright 2001-2011), in 17 pages. URL: http://www.advantecmfs.com/catalog/filt/membrane.pdf#page=11.
Protz, Kerstin: "Moderne Wundauflagen unterstutzen Heilungsprozess", Wundversorgung: Indikation und Anwendung, Geriatrie Journal, Apr. 2005, pp. 3333-3339, with translation.
Raviglione, A. et al., "Real-Time Smart Textile-Based System to Monitor Pressure Offloading of Diabetic Foot Ulcers", Journal of Diabetes Science and Technology, vol. 11, Sep. 2017, in 5 pages.
Smith & Nephew, "PICO Single Use Negative Pressure Wound Therapy System", spiral booklet, Mar. 2011, in 7 pages.
Trupp, S., "Developemt of pH-sensitive indicator dyes for the preparation of micro-patterned optical sensor layers", Sensors and Actuators B, vol. 150, Jul. 15, 2010, pp. 206-210, in 5 pages.
Aubakir, B. et al., "Vital Sign Monitoring Utilizing Eulerian Video Magnification and Thermography", 2016 38th Annual International Conference of the IEEE Engineering in Medicine and Biology Society, Aug. 16, 2016, pp. 3527-3530, in 4 pages.
Chen, C. et al., "A PNIPAM-based fluorescent nanothermometer with ratiometric readout", Chemical Communications, vol. 47, No. 3, Nov. 26, 2010, in 3 pages.
Dargaville, T. et al., "Sensors and imaging for wound healing: A review," Biosensors and Bioelectronics, vol. 41, Mar. 2013, pp. 30-42, in 13 pages.
Farooqui, M. et al., "Low Cost Inkjet Printed Smart Bandage for Wireless Monitoring of Chronic Wounds", Scientific Reports, vol. 6, Jun. 29, 2016, in 14 pages.
McLeod, A. et al., "Motion Magnification for Endoscopic Surgery", Progress in Biomedical Optics and Imaging, SPIE—International Society for Optical Engineering, Mar. 12, 2014, vol. 9036, in 8 pages.
Mohr, G. et al., "Design of acidochromic dyes for facile preparation of pH sensor layers", Anal Bioanal Chem, vol. 392, pp. 1411-1418, in 8 pages.
Reddy, T. et al., "Synthesis and Characterization of Semi-Interpenetrating Polymer Networks Based on Polyurethane and N-isopropylacrylamide for Wound Dressing", Journal of Biomedical Materials Research Part B: Applied Biomaterials, vol. 88B, No. 1, Sep. 8, 2008, in 9 pages.
Uchiyama, S. et al., "Fluorescent molecular thermometers based on polymers showing temperature-induced phase transitions and labeled with polarity-responsive benzofurazans", Analytical Chemistry, Amercial Chemical Society, vol. 75, No. 21, Oct. 4, 2003, in 10 pages.

* cited by examiner

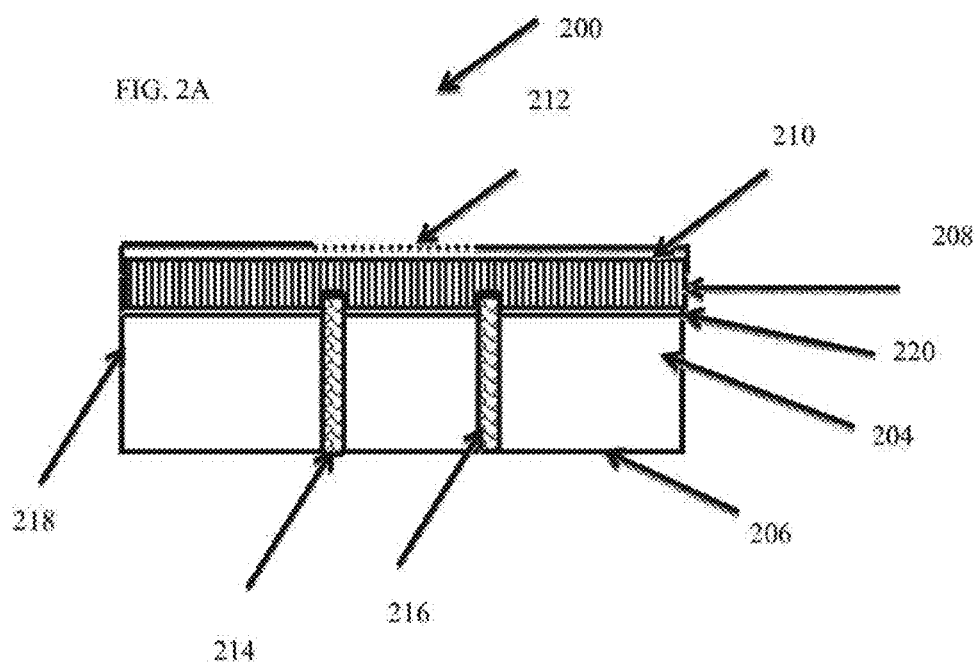
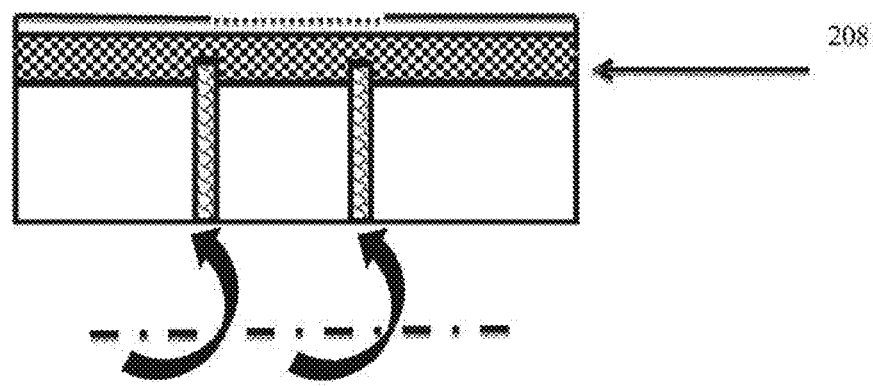

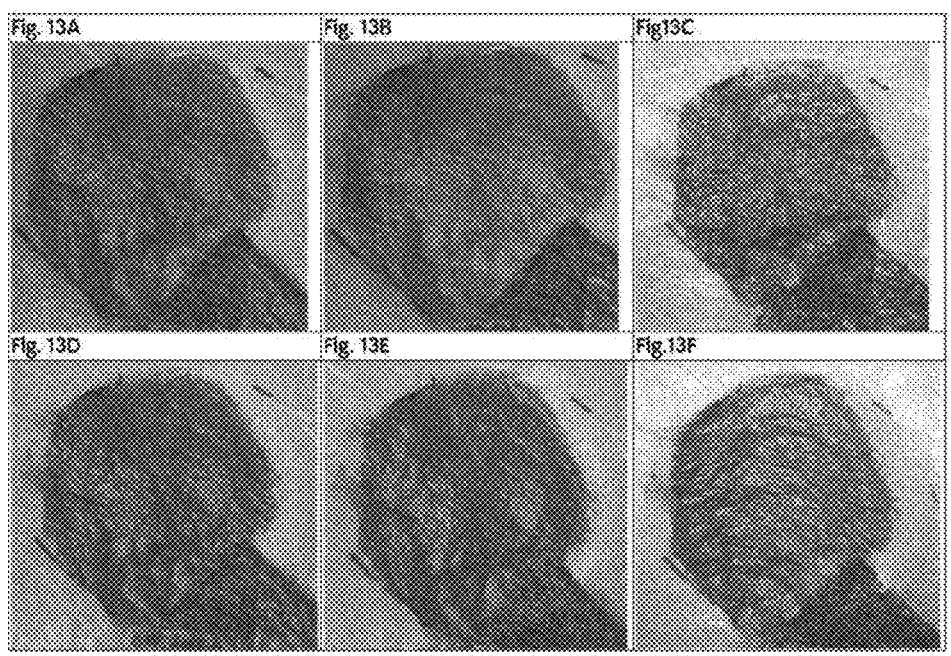

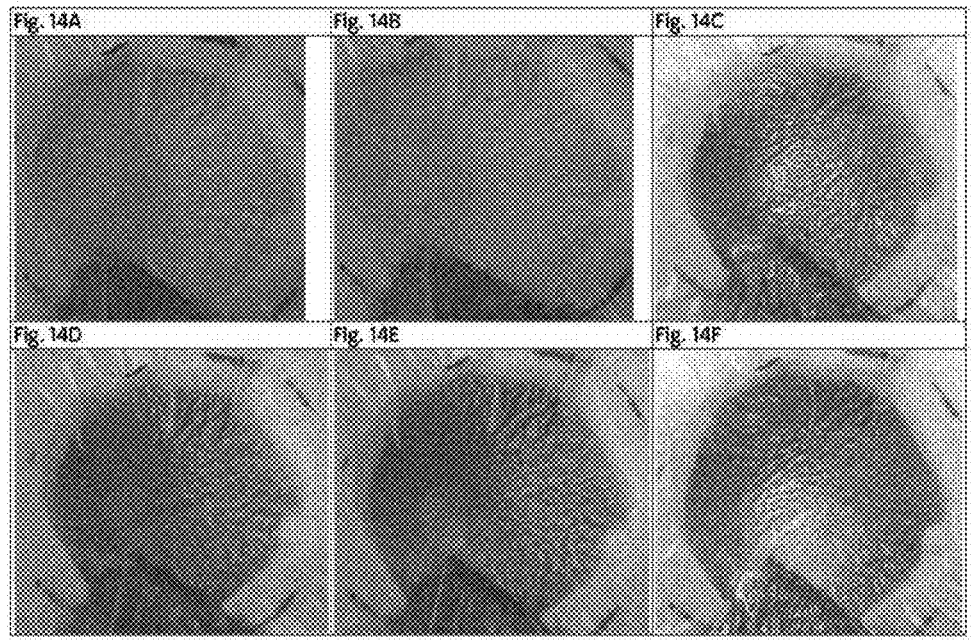
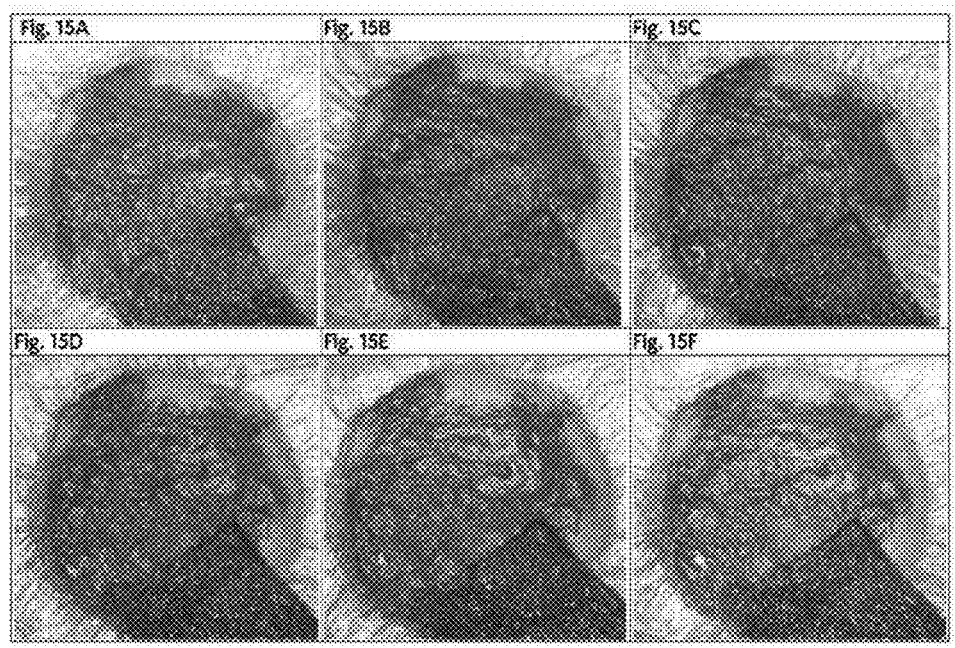

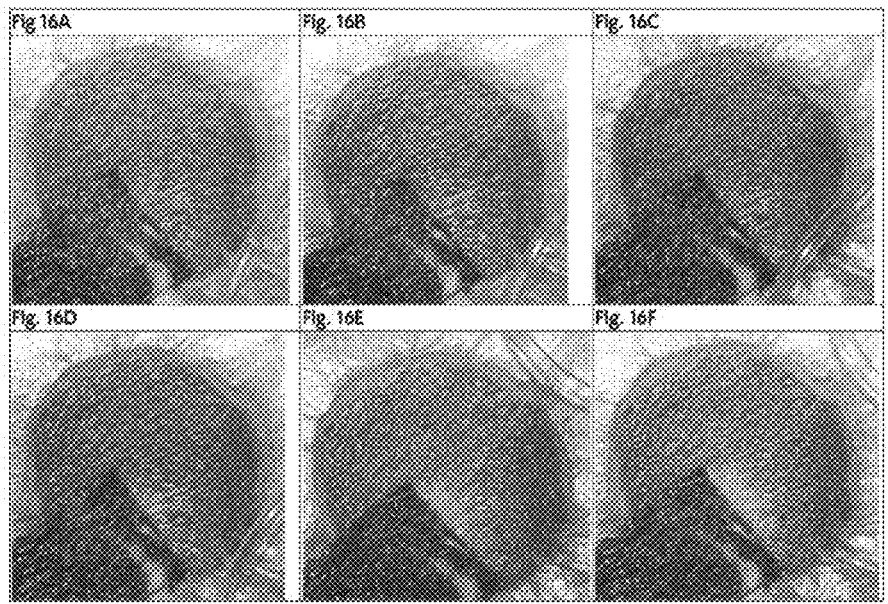
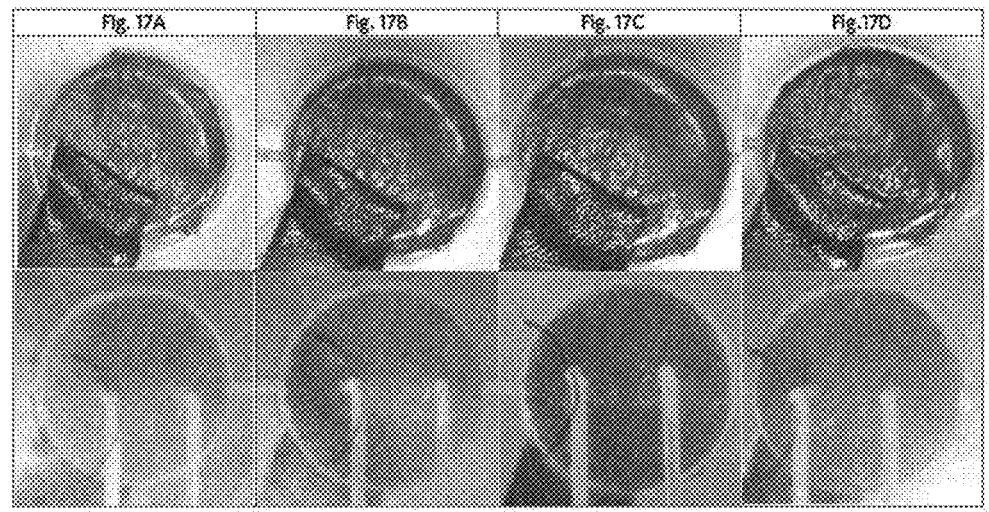

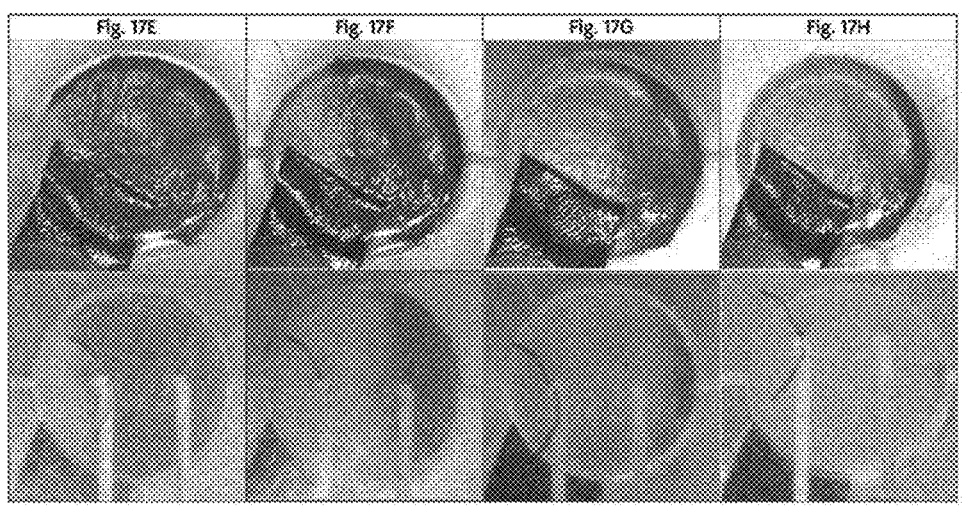

PH INDICATOR DEVICE AND FORMULATION

CROSS REFERENCE TO RELATED APPLICATIONS

This application is a continuation of U.S. application Ser. No. 14/650,547, filed Jun. 8, 2015, which is a 371 of International Application No. PCT/EP2014/071520, filed Oct. 8, 2014, which claims the benefit of United Kingdom Application No. 1317746.4, filed Oct. 8, 2013. The entire contents of the above applications are incorporated herein by reference.

BACKGROUND

The need to reliably test the pH of a fluid sample is a requirement in a plethora of industries, particularly where the pH is indicative of potential quality, safety or health concerns. pH measurements are important in, for example, medicine, biology, chemistry, agriculture, forestry, food science, environmental science, oceanography, civil engineering, chemical engineering, nutrition, water treatment and water purification.

The pH of water is routinely tested. The pH of drinking water is routinely monitored to ensure that it is safe to drink, whereas the water in swimming pools is routinely tested to ensure that it is safe to swim in. Monitoring alterations in the pH of fish ponds or river water can be indicative of environmental pollution. In agriculture and horticulture, knowledge of the pH of the soil is not only instructive in the selection of suitable crops but also discerns whether there are local environmental issues, such as pollution. In the food and brewing industries, maintaining a proper pH range is essential in many of the physical and chemical reactions that take place during food and drink processing. Monitoring the pH of bodily fluids can be a useful diagnostic. For example, it has been demonstrated that the pH of saliva can predict susceptibility to a range of diseases, including cancer, heart disease and osteoporosis.

pH testing is conventionally performed using pH meters, but these are impractical for a variety of applications as they require regular calibration using standard buffer solutions. Furthermore, the glass electrodes are fragile and must be kept constantly wet, normally in an acidic solution, in order to avoid dehydration of the pH sensing membrane and subsequent dysfunction of the electrode. Disposable pH test strips are available, but due to the permanence of the colour change as a function of pH of the test sample, the strips are unable to demonstrate any changes in pH over time. Additionally, the disposable characteristic adds to the cost implications.

A need exists for a device which enables the real-time, reversible and stable detection of pH in a fluid.

SUMMARY

This application discloses devices and methods related to devices having pH indicators for monitoring the pH of a fluid. Other advantages and improvements will be apparent to one of skill in the art upon review of the application.

In one aspect, a device is provided for determining pH of a fluid sample. The device preferably includes a surface configured to contact the fluid and a pH indicator covalently immobilised thereon, wherein the pH indicator has a first colour prior to contact with the fluid and changes colour along a colour spectrum as a function of the pH of the fluid.

In embodiments, the pH indicator changes colour in response to change in pH and this colour change is detectable at, for example, intervals of about a 0.1 unit, about 0.2 unit, about 0.3 unit about 0.4 unit or about 0.5 unit interval of pH. It is envisaged that the detection level will vary based on the type of detection means utilised. For example, an electronic detector such as a colour meter capable of detecting changes in colour of light, has the capability to detect a 0.1 unit change in pH. In comparison, the human eye is only capable of visually detecting a colour change which is associated with about a 0.5 unit change in pH. In embodiments, the pH indicator utilised in the device is able to detect the pH between about pH 0 and about pH 14 and indicates changes in pH by way of a colour change along a colour spectrum, with each colour in the spectrum being associated with a particular pH. In embodiments, the pH indicator is able to detect a pH between about pH 5.0 and about pH 10.0. In embodiments, the pH indicator is able to detect a pH between about pH 5.5 and about pH 9.5. More particularly the pH indicator is able to detect a pH between about pH 6.5 and about pH 9.5. Suitable pH indicators include phenylazo compounds such as those listed in Table 1 which are available from Fraunhofer EMFT, Germany.

TABLE 1

| Phenylazo compounds | |
| --- | --- |
| Code | Chemical name |
| GJM-514 | 2-[4(2-hydroxyethylsulfonyl)-phenyl]diazenyl]-4-methylphenol |
| GJM-546 | 1-hydroxy-4-[4[(hydroxyethylsulphonyl)-phenylazo]-napthalene-2-sulphonate |
| GJM-492 | 2-fluoro-4-[4[(2-hydroxyethanesulphonyl)-phenylazo]-6-methoxy phenol |
| GJM-534 | 4-[4-(2-hydroxyethylsulphonyl)-phenylazo]-2,,6-dimethoxyphenol |

In some embodiments, the pH indicator is a triarylmethane dye. In some embodiments, the pH indicator is a fluorescent dye.

In embodiments, the pH indicator comprises a combination of compounds which allows a broader pH range to be detected than can be detected by use of a single compound. For example, the pH indicator comprises a combination of phenylazo compounds. In embodiments, the combination comprises at least two phenylazo compounds selected from the group listed in Table 1. In embodiments the combination comprises at least three phenylazo compounds selected from the group listed in Table 1. In embodiments, the combination comprises at least one phenylazo compound selected from the group listed in Table 1 and at least one compound that is not a phenylazo compound. In embodiments, derivatives or modifications of the phenylazo compounds listed in Table 1 are envisaged.

In embodiments, the device is a cellulosic material, for example a cellulose pad. In embodiments, the device is a non-woven mesh or perforated film.

In some embodiments, the fluid is a liquid. Non-limiting examples includes water. In some embodiments, the fluid is a gas, for example for use in a face mask. In some embodiments, the fluid is a moisture. Non-limiting examples include the moisture associated with a soil sample. In some embodiments, the fluid is a bodily sample. Non-limiting examples include, saliva, urine, blood, sweat/perspiration.

In another aspect, a device is provided for determining pH of a fluid sample. The device preferably includes: (a) a fluid-contacting surface, (b) an opposing non-fluid contacting surface, (c) a pH indication zone comprising a pH indicator covalently immobilised therein which indicates the pH of a fluid, wherein the colour of the pH indicator changes in response to a change in the pH of the fluid, and (d) at least one conduit for directing fluid towards the pH indication zone. The conduit helps direct fluid toward the pH indicator without materially altering the pH en route to the indicator. In certain embodiments, the material of the conduit contains no acid or base functionality, that is to say, it is neutral and can not remove any acid or base entities from the fluid until it reaches the pH indicating system. In certain embodiments, the device has an outer surface and the pH indication zone is located at or near the outer surface. In other embodiments, the device has a peripheral edge extending between the fluid contacting surface and the opposing non-fluid contacting surface and pH indication zone is located at or near to this peripheral edge. In certain embodiments, the conduit directs fluid laterally towards the pH indication zone. In embodiments, the pH indicator changes colour in response to change in pH and this colour change is detectable at, for example, intervals of about a 0.1 unit, about 0.2 unit, about 0.3 unit about 0.4 unit or about 0.5 unit interval of pH. It is envisaged that the detection level will vary based on the type of detection means utilised. For example, an electronic detector such as a colour meter has the capability to detect a 0.1 unit change in pH. In comparison, the human eye is only capable of visually detecting a colour change which is associated with about a 0.5 unit change in pH. In embodiments, the pH indicator utilised in the device is able to detect the pH between pH 0 and 14 and indicates changes in pH by way of a colour change along a colour spectrum, with each colour in the spectrum being associated with a particular pH. In embodiments, the pH indicator is able to detect pH between about pH 5 and about pH10. Particularly, the pH indicator is able to detect pH between about pH 5.5 and about pH 9.5. More particularly, the pH indicator is able to detect pH between about pH 6.5 and about pH 9.5. Suitable pH indicators include phenylazo compounds such as those selected from the group listed in Table 1. In embodiments, the pH indicator comprises a combination of compounds which allows a broader pH range to be detected than can be detected by use of a single compound. For example, the pH indicator comprises a combination of phenylazo compounds. In embodiments, the combination comprises at least two phenylazo compounds selected from the group listed in Table 1. In embodiments, the combination comprises at least three phenylazo compounds selected from the group listed in Table 1. In embodiments, the combination comprises at least one phenylazo compound selected from the group listed in Table 1 and at least one compound that is not a phenylazo compound. In embodiments, derivatives or modifications of the phenylazo compounds listed in Table 1 are envisaged.

In a further aspect, a formulation is provided for indicating pH of a fluid. Advantageously, the pH indicator is covalently immobilised within the formulation and is therefore not washed away by the fluid upon contact. The formulation preferably includes a dye that functions as a pH indicator. The dye may include a phenylazo compound, where the colour of the phenylazo compound changes in response to a change in the pH of the fluid. In embodiments, the pH dye changes colour in response to a 0.5 unit interval change in pH. For example, the pH indicator has a different colour for each 0.5 unit interval change in pH. The pH indicator utilised in the device is able to detect the pH between pH 5 and 10, particularly between pH 5.5 and 9.5 and more particularly between pH 6.5 and 9.5. Suitable pH indicators include phenylazo compounds such as those selected from the group listed in Table 1. In embodiments, the pH indicator comprises a combination of compounds which allows a broader pH range to be detected than can be detected by use of a single compound. For example, the pH indicator comprises a combination of phenylazo compounds. In embodiments, the combination comprises at least two phenylazo compounds selected from the group listed in Table 1. In embodiments, the combination comprises at least three phenylazo compounds selected from the group listed in Table 1. In embodiments, the combination comprises at least one phenylazo compound selected from the group listed in Table 1 and at least one compound that is not a phenylazo compound. In embodiments, derivatives or modifications of the phenylazo compounds listed in Table 1 are envisaged. In embodiments, the formulation is applied to a device for use in detecting pH at the point of manufacture. In embodiments, the formulation is an adhesive. In embodiments, the adhesive is a low tack adhesive, for example a silicon adhesive. In other embodiments, it is envisaged that the formulation is a gel, for example, a conformable semi-rigid or rigid gel, that does not disintegrate upon contact with the fluid to be tested. The formulation can be used in a device according to the first and/or second aspect.

In another aspect, a method is provided for monitoring the pH of a fluid. The method preferably comprises the steps of: (a) providing a device comprising a surface configured to contact the fluid, said surface having a pH indicator covalently bound thereto, wherein the pH indicator has a first colour prior to contact with the fluid and changes colour as a function of the pH of the fluid, (b) contacting the device with the fluid, (c) assessing the colour of the pH indicator. It is envisaged that the method can be utilised in numerous applications in which the knowledge of the pH of a fluid sample is paramount to determining quality control or safety. Non-limiting examples of potential applications include: food storage; packaging spoilage indicators; wine; brewing; analysis of drinking water, swimming pool water, river water or fish ponds; agriculture and horticulture; clothing, for example perspiration analysis; in-line monitoring of processes, gases, liquids; skin care—medical (dermatology) or cosmetic; coatings of containers and surfaces to detect changes/inconsistencies; monitoring drug release or stability.

In a further aspect, a device comprises a fluid contacting surface having a pH indicating means covalently bound thereto, wherein the pH indicating means has a first colour prior to contact with a fluid and changes colour as a function of the pH of the fluid.

In another aspect a device comprises a pH indicating means, wherein the pH indicating means has a first colour prior to contact with a fluid and changes colour as a function of the pH of the fluid and a conduit means for directing the fluid towards the pH indicating means.

Variations and modifications of these embodiments will occur to those of skill in the art after reviewing this disclosure. The foregoing features and aspects may be implemented, in any combination and sub-combinations (including multiple dependent combinations and sub-combinations), with one or more other features described herein. The various features described or illustrated above, including any components thereof, may be combined or integrated in other systems. Moreover, certain features may be omitted or not implemented.

Further areas of applicability of the disclosed devices and methods will become apparent from the detailed description provided hereinafter. It should be understood that the detailed description and specific examples, while indicating particular embodiments, are intended for purposes of illustration only and are not intended to limit the scope of the disclosure or any of the claims that may be pursued.

DESCRIPTION OF THE DRAWINGS

The foregoing and other objects and advantages will be appreciated more fully upon consideration of the following detailed description, taken in conjunction with the accompanying drawings, in which like reference numbers refer to like parts throughout. These depicted embodiments are to be understood as illustrative and not limiting in any way:

FIGS. 2A and 2B are side cross-sectional views of an illustrative device in which a fluid is guided via a conduit to a pH indication zone which includes a pH indicator, the colour of the indicator changes as an indication of the pH of the fluid.

FIGS. 13 A-F are photographs of pH sensitive gauze in ex-vivo wound model with alternating pH 5 and pH 8 horse serum being pumped in.

FIG. 13A is a photograph of pH5 after 2.5 hours approx.
FIG. 13B is a photograph of pH5 after 5.5 hours approx.
FIG. 13C is a photograph of pH 8 after 8 hours approx.
FIG. 13D is a photograph of pH 5 after 3.5 hours approx.
FIG. 13E is a photograph of pH 5 after 5.5 hours approx. with the flow rate of horse serum increased at 3.5 hours.
FIG. 13F is a photograph of pH 5 after 7.5 hours with the flow rate of horse serum increased at 3.5 hours and at 5.5 hours.

FIG. 14A to F are photographs of pH sensitive foam (V.A.C. WhiteFoam trade mark of KCT) in an ex-vivo wound model with alternating pH5 and pH 8 horse serum being pumped in.

FIG. 14A is a photograph at pH 5 after 2.5 hours approx.
FIG. 14B is a photograph at pH 5 after 5.5 hours approx.
FIG. 14C is a photograph at pH 8 after 15 hours approx.
FIG. 14D is a photograph at pH 5 after 3.5 hours approx.
FIG. 14E is a photograph at pH 5 after 5.5 hours approx., with the flow rate of horse scrum increased at 3.5 hours.
FIG. 14F is a photograph at pH 5 after 7.5 hours approx., with the flow rate of horse serum increased at 3.5 hours and at 5.5 hours.

FIG. 15 A to E are photographs of pH sensitive gauze in an ex-vivo wound model with alternating basic and acidic water being pumped in.

FIG. 15A is a photograph at 8 am Day 1 showing basic pH.
FIG. 15B is a photograph at 12:57 pm Day 1 (5 hours) showing basic pH.
FIG. 15C is a photograph at 08:03 am Day 2 (24 hours) showing basic pH.
FIG. 15D is a photograph at 12:41 pm Day 2 (5 hours) showing acidic pH.
FIG. 15E is a photograph at 15:06 Day 2 (7 hours) showing acidic pH.
FIG. 15F is a photograph at 16:47 Day 2 (9 hours) showing acidic pH.

FIG. 16A to F are photographs of pH sensitive foam in an ex-vivo wound model with alternating basic and acidic water being pumped in.

FIG. 16A is a photograph at 8 am Day 1 showing basic pH.
FIG. 16B is a photograph at 12:57 pm Day 1 (5 hours) showing basic pH.
FIG. 16C is a photograph at 08:03 am Day 2 (24 hours) showing basic pH.
FIG. 16D is a photograph at 09:06 Day 2 (1 hour) showing acidic pH.
FIG. 16E is a photograph at 15:06 Day 2 (7 hours) showing acidic pH.
FIG. 16F is a photograph at 16:47 Day 2 (9 hours) showing acidic pH.

FIG. 17A to H are photographs of pH sensitive foam in a clear Perspex wound model with alternating basic and acidic water.

FIG. 17A is a photograph at 8 am Day 1 showing basic pH.
FIG. 17B is a photograph at 12:56 Day 1 (5 hours) showing basic pH.
FIG. 17C is a photograph at 16:20 Day 1 (8.5 hours) showing basic pH.
FIG. 17D is a photograph at 8:02 am Day 2 (24 hours) showing basic pH.
FIG. 17E is a photograph at 09:05 am Day 2 (1 hour) showing acidic pH.
FIG. 17F is a photograph at 10:50 am Day 2 (3 hours) showing acidic pH.
FIG. 17G is a photograph at 13:26 Day 2 (5.5 hours) showing acidic pH.
FIG. 17H is a photograph at 15:05 Day 2 (7 hours) showing acidic pH.

DETAILED DESCRIPTION

To provide an understanding of the devices and methods describe herein, certain illustrative embodiments and examples will now be described.

Figure 1A:
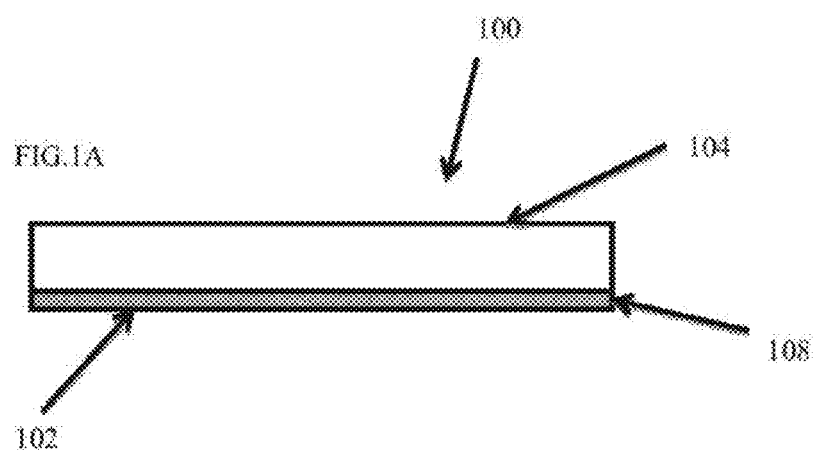
FIGS. 1A and 1B are side cross-sectional views of an illustrative device having a pH indicator, the colour of which changes as a result of alterations in the pH of a fluid.
Figure 1B:
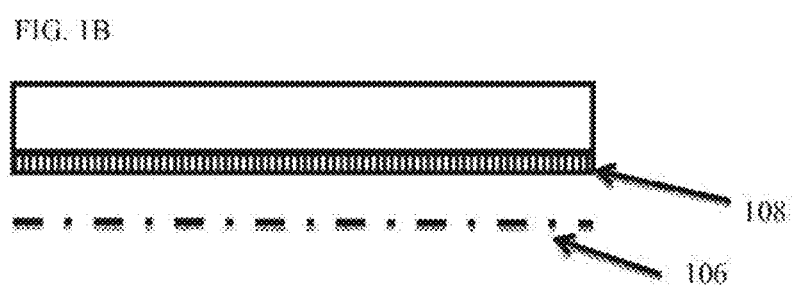

FIG. 1A depicts a device 100 having a fluid-contacting surface 102 and an opposing non-fluid-contacting surface 104. FIG. 1B depicts the device 100 being brought into contact with a fluid 106. The device 100 can be made of any material that is suitable for contact with the fluid without disintegrating.

The device further includes a pH indicator 108 which is applied to one or both of surfaces 102 and/or 104. The pH indicator is covalently immobilised on or adjacent to the surface 102 and/or 104 so that it is not washed away by the fluid.

In embodiments, the pH indicator is chemically bound to the surface 102 and/or 104. For example, the pH indicator is covalently bound directly to the surface 102 and/or 104. In alternative embodiments, the surface 102 and/or 104 is provided within an adhesive and the pH indicator is covalently bound to reactive moieties within the adhesive. For example, a conventional acrylic adhesive, such as K5 (Smith & Nephew, Inc) used in the construction of wound dressings contains residues of 2-hydroxy-ethylmethacrylate, which provide a reactive functional hydroxyl (OH) group, pendant to the polymer backbone, to which the pH indicator can be covalently bound. Other suitable adhesives include acrylic-based adhesives with pendant OH or COOH groups.

In embodiments on which the pH indicator is only applied to one surface of a non-porous device, then an indication, for indicating which side the pH indicator is applied to may be provided. This indication allows the user to appropriately orient the device during placement on or in the fluid to ensure that the surface which has the pH indicator is correctly orientated and comes into contact with the fluid.

The pH indicator may be applied across substantially the entire surface 102 and/or 104, to allow any variations in the pH at the meniscus of the fluid sample to be identified. Alternatively, the pH indicator may be applied to discrete areas of surfaces 102 and/or 104. The pH indicator exhibits a first colour prior to contact with a fluid and changes colour as a function of the pH of the fluid. The first colour of the pH indicator may be colourless.

The pH indicator is capable of reversibly changing colour in response to pH. In embodiments, the pH indicator is a phenylazo compound. In certain embodiments, the phenylazo compound is selected from the group listed in Table 1. In some embodiments, the phenylazo compound is not 2-[4(2-hydroxyethylsulfonyl)-phenyl]diazenyl]-4-methylphenol. In some embodiments, the phenylazo compound is not hydroxy-4-[4[(hydroxyethylsulphonyl)-phenylazo]-napthalene-2-sulphonate. In some embodiments, the phenylazo compound is not 2-fluoro-4-[4[(2-hydroxyethanesulphonyl)-phenylazo]-6-methoxy phenol. In some embodiments, the phenylazo compound is not 4-[4-(2-hydroxyethylsulphonyl)-phenylazo]-2,6-dimethoxyphenol. In certain embodiments, the phenylazo compound is 2-[4(2-hydroxyethylsulfonyl)-phenyl]diazenyl]-4-methylphenol. In some embodiments, the pH indicator includes a plurality of phenylazo compounds. In some embodiments, the pH indicator includes a combination of phenylazo compounds, for example a combination of phenylazo compounds selected from the group listed in Table 1. In some embodiments, the pH indicator includes a combination of two phenylazo compounds. In some embodiments, the pH indicator includes a combination of three phenylazo compounds. In some embodiments, 2-[4(2-hydroxyethylsulfonyl)-phenyl]diazenyl]-4-methylphenol is combined with at least one other phenylazo compound selected from the group listed in Table 1. The ratio of phenylazo compound may be 1:1, but other ratios are envisaged, for example, but in no way limiting, 0.5:1.5 or 1.5:0.5 or 1:2 or 2:1 or 1:0.1. In alternative embodiments, the pH indicator includes at least one phenylazo compound, for example a phenylazo compound selected from the group listed in Table 1 and at least one other compound that is not a phenylazo compound. In certain embodiments, the pH indicator is not a phenylazo compound.

FIGS. 2 A&B illustrate a device in which temporal changes in pH can be monitored whilst the device is in situ. FIG. 2A shows a side cross-sectional view of a device 200 comprising an absorbent element 204, the lower surface of which is a fluid-contacting surface 206. The device also comprises a pH indication zone 208 which is located at or adjacent to the opposing non fluid-contacting surface 210. This pH indication zone includes a pH indicator (e.g., as disclosed herein) which is capable of reversibly changing colour in response to changes in pH. In this illustrated embodiment, the pH indication zone 208 is disposed above the absorbent layer 204, so the pH indicator can be monitored over time without having to remove the device from any substrate that it is adhered to.

A transparent layer 212 overlays at least part of the pH indication zone, which protects the integrity of the pH indicator but still allows the user to monitor the colour of the pH indicator over time. The device includes at least one conduit that is configured to direct fluid to the pH indication zone 206, ensuring that the pH of the fluid is not materially altered as it passes through the components of the device. One or a plurality of conduits could be used. As shown in FIGS. 2 A&B, two conduits are used, although one or more other conduits could also be included. The two conduits 214 and 216 are oriented vertically and extend across the device. The conduits are preferably sealed, so as to not exchange fluid with the absorbent layer, but are in communication with the pH indication zone 208 and direct the fluid to the pH indication zone 208 located in the upper part of the device. The conduits may be in the form of narrow capillaries which transmit the fluid towards the pH indication zone 208. The conduits may incorporate or may be formed from wicking materials, for example, woven, non-woven, knitted, tows or fibres made of suitable materials to facilitate wicking of the fluid towards the pH indication zone 208. In alternative embodiments, a pH indication zone is provided at or near a lateral edge 218 or 220 of the device and at least one conduit is provided within the device to direct the fluid laterally to the pH indication zone. In some embodiments, the pH indication zone is provided in a layer of the device which forms an outer surface of the device and a transparent cover layer is not used. In some embodiments, the conduits may take the form of a long strip or be of an elongated lozenge shape when viewed from the fluid-contacting surface. Alternatively, the conduit may be formed of crosses or quadrilateral shapes.

Methods of immobilising a phenylazo dye on the devices illustrated in FIGS. 1 and 2 are also contemplated. An example includes the following steps:

In a first step, 25 mg of a phenylazo pH indicating dye, for example a phenylazo pH indicating dye selected from the group listed in Table 1, is reacted with 140 µl concentrated sulphuric acid for 30 mins to form a dye solution.

In a second step, 200 ml of distilled water is added to the dye solution formed in the first step.

In a third step, 406 µl of a 32% w/v solution of sodium hydroxide is added to the solution formed in the second step.

In a fourth step, 25.45 ml of a 2.36M solution of sodium carbonate is added to the solution formed in the third step.

In a fifth step, 1.35 ml of a 32% w/v solution of sodium hydroxide is added to the solution formed in the fourth step and the volume made up to 250 ml with distilled water.

In a sixth step, a material on which the pH indicating dye is to be bound is placed in the solution and left to react for approximately 1-2 hours. Examples of suitable materials include, but are not limited to: TENCEL fibres of the Durafiber product, polyurethane foam of the Allevyn product, cellulose pad of the Opsite Post-op product, or K5 adhesive-coated polyurethane film, all available from Smith & Nephew, Inc. The material is then washed with distilled water until no dye is released. The material is then dried.

EXAMPLES

Figure 3:
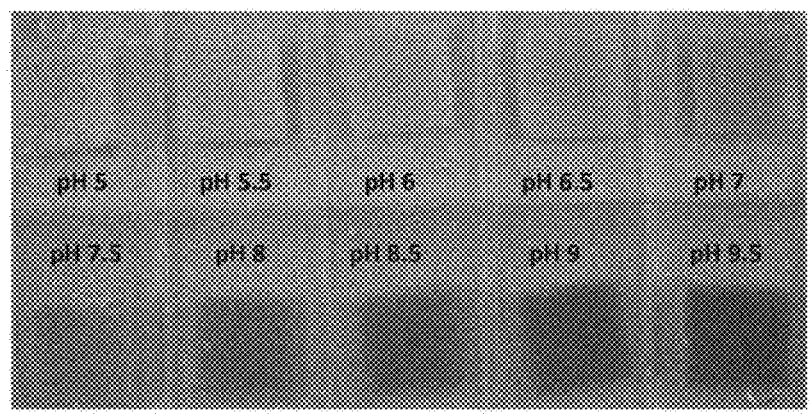
FIG. 3 is a photograph of a Post-Op sample dyed with GJM-514, illustrating changes in colour of the dye in response to solution changing pH along a pH unit interval scale.

A sample of the pad from an Opsite Post-Op dressing (Smith & Nephew, Inc) was prepared in different samples, and each sample was covalently bound with one or a combination of phenylazo dyes, selected from GJM-514, GJM-492, GJM-546, and GJM-534. The structures of these dyes are shown in Table 1. It was discovered that these dyes had colour-changing characteristics that varied according to changes in pH. The Post-Op samples were covalently bound with GJM-514 alone or with GJM-514 combined with one of GJM-492, GJM-546 and GJM-534 using the method as described above in relation to FIGS. 1-3. The Post-Op material was exposed to buffered solutions having a pH of 5, 5.5, 6, 6.5, 7, 7.5, 8, 8.5, 9 and 9.5. Photographs were taken of each sample to demonstrate the visible changes in colour. A colour pen (for example, Dr Lange Colour Pen), a pen-type colorimeter was used to detect marginal colour changes which are undetectable by the human eye. Colour pen measurements include, but are not limited, to three different readings: the L*, a* and b* values.

L* represents the lightness/luminosity of the colour
   L*=0 is black
   L*=100 is diffuse white
a* is the colour's position between red/magenta and green
   A positive a* value indicates magenta
   A negative a* value indicates green
b* is the colours position between yellow and blue
   a positive b* value indicates yellow
   a negative b* value indicates blue Example 1: Post-Op Pad Dyed with GJM-514

A sample of the pad from an Opsite Post-Op dressing (Smith & Nephew) was covalently bound with the dye GJM-514 was exposed to buffered solutions at pH 5 pH 9.5. The panel of photographs in FIG. 3 demonstrates the colour change of GJM-514 over this pH range, going from yellow in colour (at pH5) to pink (at pH 9.5).

Table 2 illustrates the colour pen measurements (L*, a* and b*) of the colour of the GJM-514 dye over a pH range of pH 5-pH 9.5. An optimal dye for use as a pH indicator is one which demonstrates a linear change in a measurement of a specific parameter of colour (for example L*, a* or b*) over a broad pH range. Outside of the linear region, the dye is either unable to change colour in response to a change in pH or the change in colour is so minimal that it is undetectable.

TABLE 2

| pH | L* | a* | b* |
|---|---|---|---|
| 5 | 63.3 | −1.9 | 41.5 |
| 5.5 | 69.2 | 0.3 | 36.2 |
| 6 | 65.7 | 1.4 | 35.1 |
| 6.5 | 59.3 | 1.2 | 35.5 |
| 7 | 56.9 | 2 | 33.6 |
| 7.5 | 55.4 | 4.8 | 30.6 |
| 8 | 46.8 | 10.4 | 21.4 |
| 8.5 | 43.3 | 15.6 | 15.4 |
| 9 | 40.2 | 21.3 | 8.7 |
| 9.5 | 37.5 | 24.8 | 4.9 |

Figure 4A:
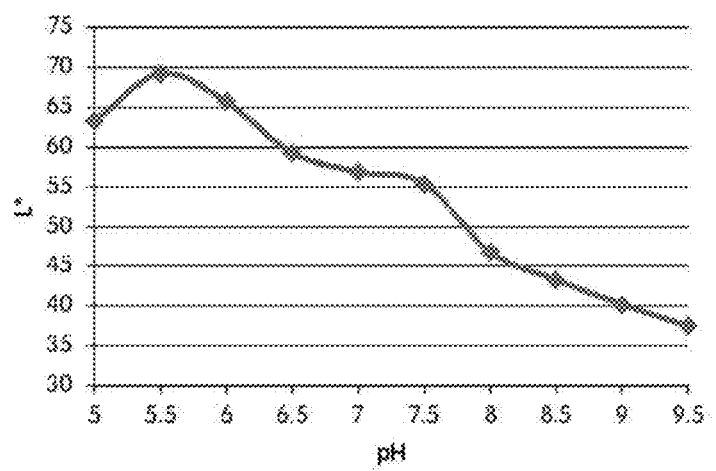
FIGS. 4A-F are graphic representations of colour pen measurements for the Post-Op sample illustrated in FIG. 3.
Figure 4B:
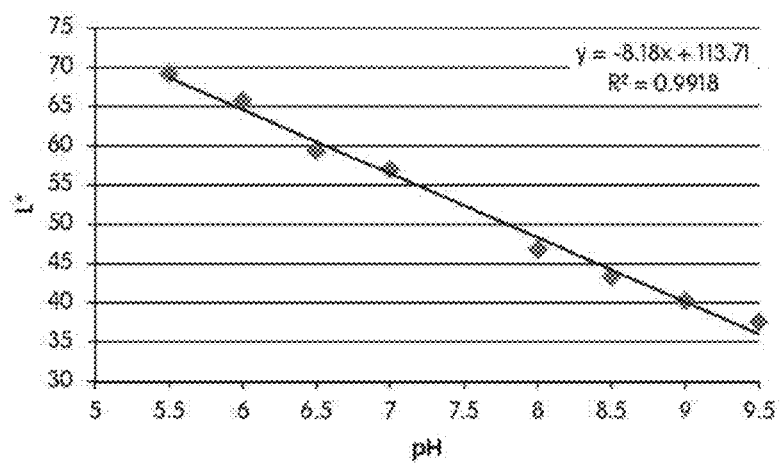

FIGS. 4A and 4B illustrate the L* measurements taken of the GJM-514 dye with the colour pen presented graphically. The L* results of FIG. 4A show that the L* value decreases from pH 5.5 to pH 9.5 as the luminosity of the dye decreases relative to the increasing pH. These results have also been plotted in FIG. 4B and demonstrate a linear region between pH 7.5 and 9.5. The trend line has a gradient of −8.18 and an $R^2$ value of 0.9918.

Figure 4C:
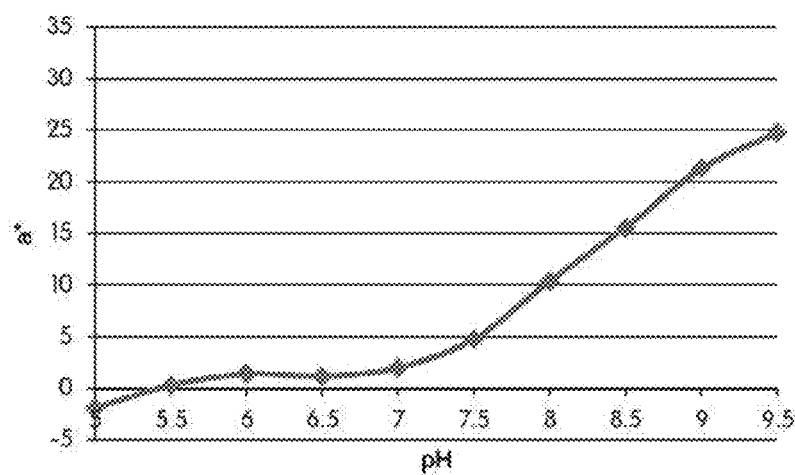
Figure 4D:
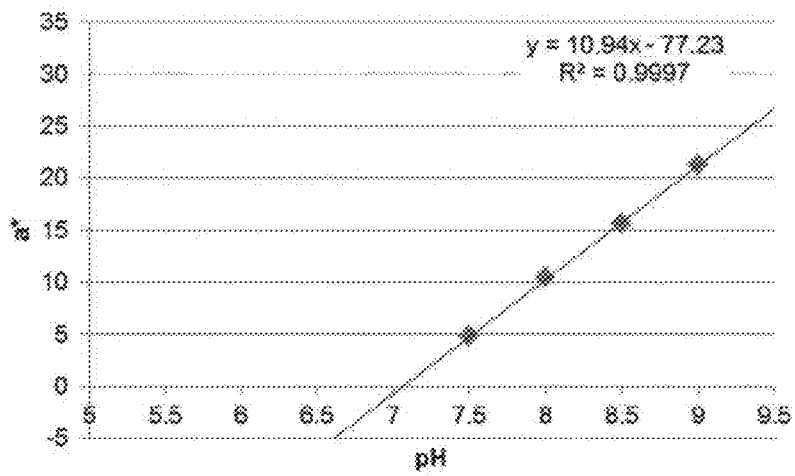

FIGS. 4C and 4D illustrate the a* measurements taken of the GJM-514 dye with the colour pen presented graphically. FIG. 4C illustrates the a* measurements taken at various pH values between pH 5-pH 9.5. FIG. 4D illustrates the a* measurements at various pH values over the linear portion of the trend line, between pH 7.5 and 9. The trend line has a gradient of 10.94 and an $R^2$ value of 0.9997.

Figure 4E:
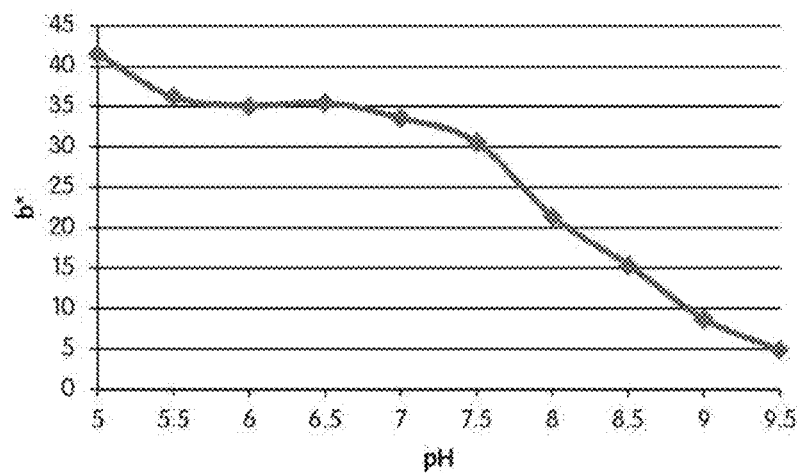
Figure 4F:
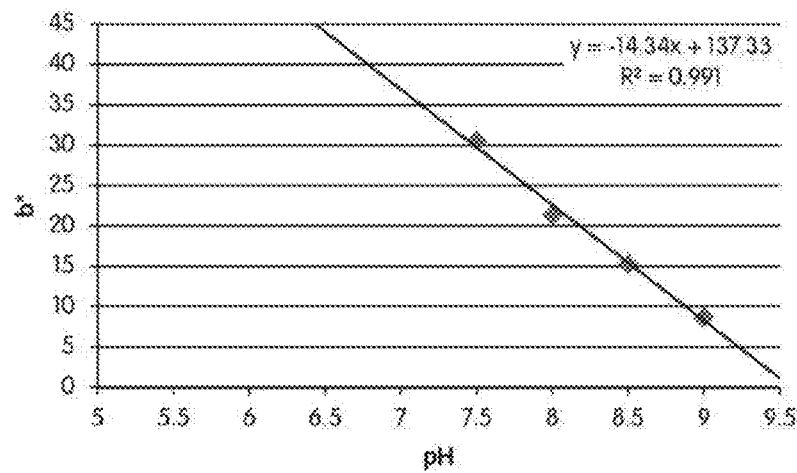

FIGS. 4E and 4F illustrate a graphical representation of the b* measurements taken of the GJM-514 dye. FIG. 4E shows the b* measurements taken at various pH values between pH 5-pH 9.5. FIG. 4E illustrates the b* measurements at various pH values over the linear portion of a trend line. From FIG. 4E it can be seen that the values are fairly consistent and steady between pH 5.5 and pH 7, and after pH 7 they start to decrease. FIG. 4F shows that the results give a linear downward trend between pH 7.5 and pH 9, with a gradient of −14.34 and an $R^2$ value of 0.991.

Taking into account the colour pen results and photographs of the samples, the most accurate working range for GJM514 is between pH 7.5 and pH 9. The linear trend line of the b* measurements has a steeper gradient (−14.34) than the a* measurements (10.94) and therefore b* would be used preferentially to give a more accurate indication of the pH of the dressing when using an optical reader rather than the human eye.

Example 2: Post-Op Pad Dyed with GJM-514:GJM-492 (1:1)

Figure 5:
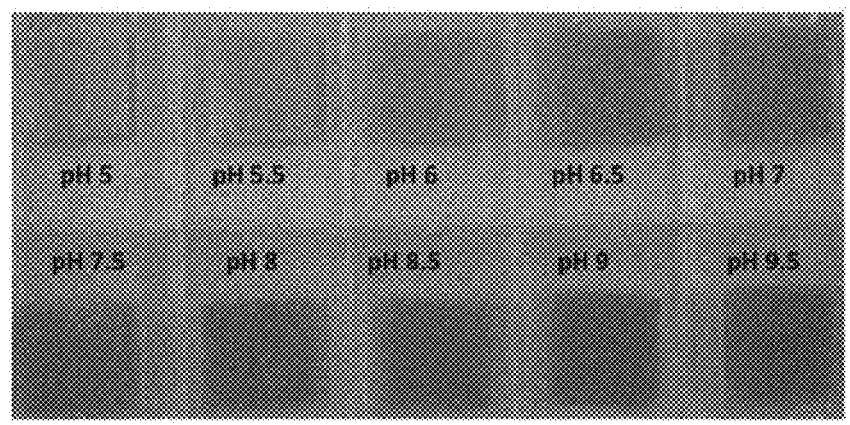
FIG. 5 is a photograph of a Post-Op sample dyed with a first combination of dyes, illustrating changes in colour of the dye combination in response to a solution changing pH along a pH unit interval scale.

A sample of the pad from an Opsite Post-Op dressing (Smith & Nephew) was covalently bound with the dye GJM-514:GJM-492 at a 1:1 ratio was exposed to buffered solutions at pH 5-pH 9.5. The panel of photographs in FIG. 5 demonstrates the colour change over this pH range, going from yellow in colour (at pH 5) to orange in colour (at pH 9.5).

Table 3 illustrates the colour pen measurements (L*, a* and b*) of the colour of the GJM-514:GJM-492 dye combination over a pH range of pH 5-pH 9.5.

TABLE 3

| pH | L* | a* | b* |
|---|---|---|---|
| 5 | 53.8 | 11.5 | 43.3 |
| 5.5 | 50.7 | 17.4 | 37.9 |
| 6 | 45.3 | 23.9 | 37.5 |
| 6.5 | 40.4 | 29.9 | 35.4 |
| 7 | 39.7 | 30.9 | 33.8 |
| 7.5 | 39.9 | 30.4 | 29.9 |

TABLE 3-continued

| pH | L* | a* | b* |
|---|---|---|---|
| 8 | 34.5 | 31.5 | 29.2 |
| 8.5 | 37.4 | 28 | 29.3 |
| 9 | 33.8 | 30.7 | 25 |
| 9.5 | 33.1 | 31.3 | 23.2 |

Figure 6A:
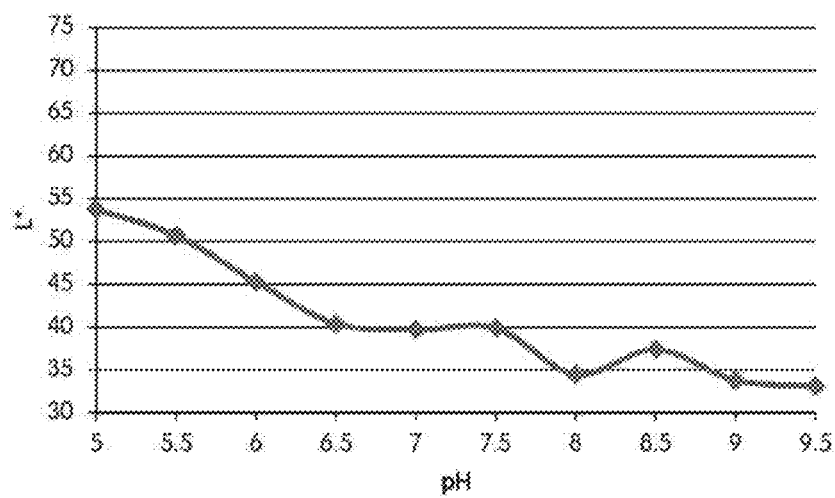
FIGS. 6A-D are graphic representations of colour pen measurements for the Post-Op sample illustrated in FIG. 5.

FIG. 6A illustrates the L* measurements taken with the colour pen presented graphically. The L* results presented in FIG. 6A show that the value for L* decreases over the range of pH 5.5 to pH 9.5 but does not follow a linear downward trend. The L* value is therefore not considered to be a reliable indicator of the colour change of this dye combination over the pH range tested.

Figure 6B:
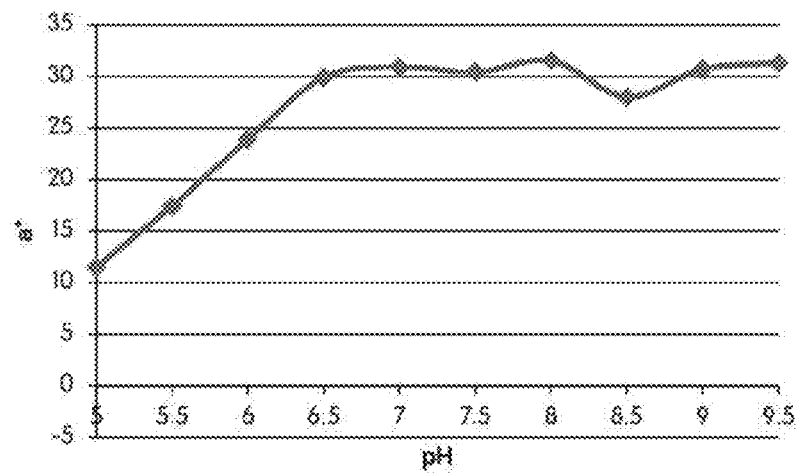
Figure 6C:
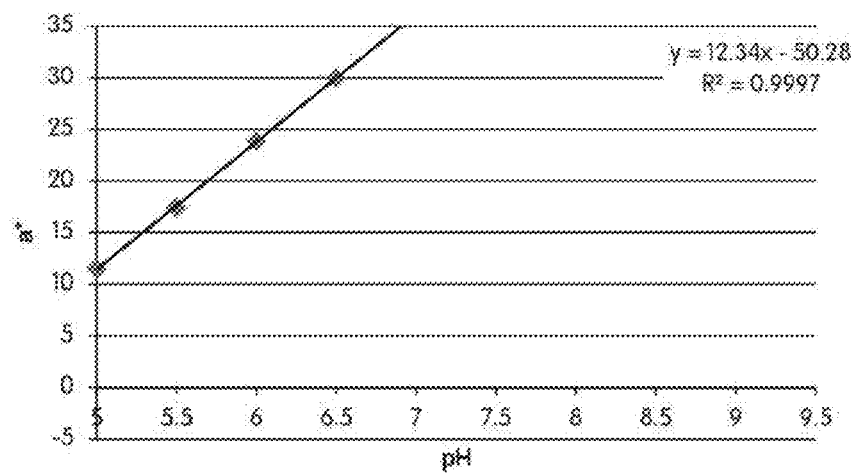

FIGS. 6B and 6C illustrate the a* measurements taken with the colour pen presented graphically. FIG. 6B illustrates the a* measurements taken at various pH values between pH 5-pH 9.5. FIG. 6C illustrates the a* measurements at various pH values over the linear portion of a trend line. An upwardly linear trend (gradient=12.34, $R^2$=0.9997) is identifiable between pH 5 and 6.5, demonstrating that there is a detectable change in colour along the red/magenta to green scale over this pH range.

Figure 6D:
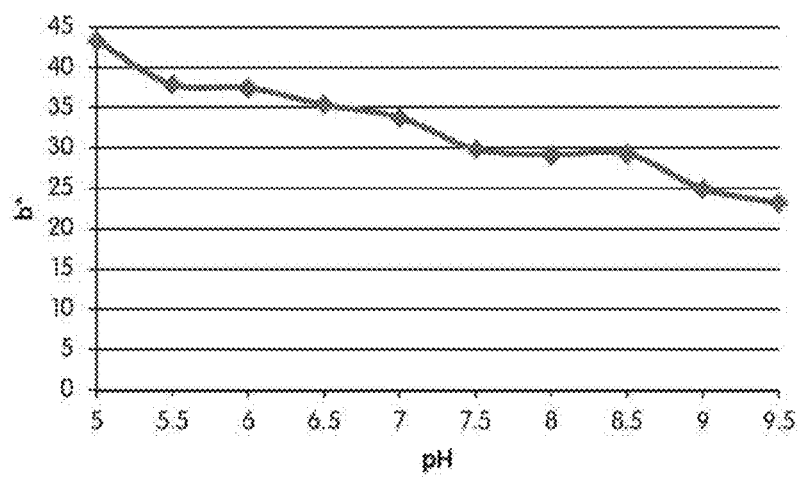

FIG. 6D illustrates a graphical representation of the b* measurements taken with the colour pen. It can be seen that there is not a significant change in b* value, but there is a downwards trend.

Taking into account the colour pen results and photographs of the samples, the working range for this dye combination appears to be between pH 5 and pH 6.5. With a* giving a useable trend line for this region that could be used to estimate the pH from the material colour.

Example 3: Post-Op Pad Dyed with GJM-514:GJM-546 (1:1)

Figure 7:
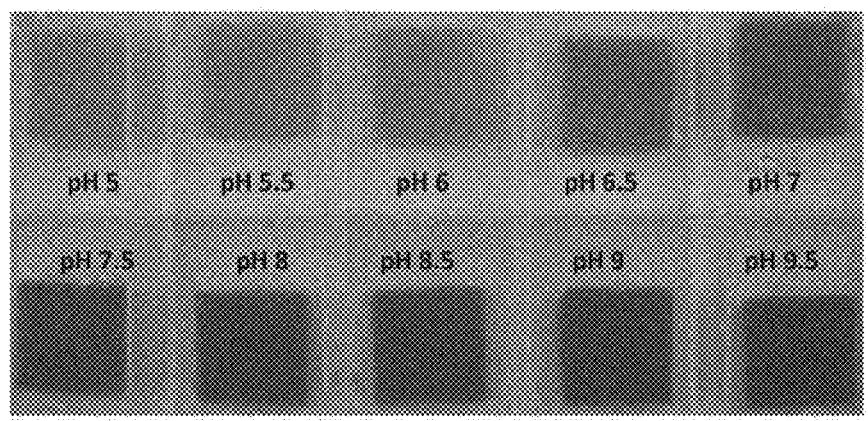
FIG. 7 is a photograph of a Post-Op sample dyed with a second combination of dyes, illustrating changes in colour of the dye combination in response to a buffered solution changing pH along a pH unit interval scale.

A sample of the pad from an Opsite Post-Op dressing (Smith & Nephew) was covalently bound with the dye GJM 514:546 at a 1:1 ratio was exposed to buffered solutions at pH 5-pH 9.5. The panel of photographs in FIG. 7 demonstrates the colour change over this pH range, going from orange in colour (at pH 5) to pink (at pH 9.5).

Table 4 illustrates the colour pen measurements (L*, a* and b*) of the colour of the GJM-514:GJM-546 dye combination over a pH range of pH 5-pH 9.5.

TABLE 4

| pH | L* | a* | b* |
|---|---|---|---|
| 5 | 45.7 | 22.7 | 44.1 |
| 5.5 | 43.4 | 22.8 | 40.1 |
| 6 | 43.9 | 24.8 | 34.6 |
| 6.5 | 36.5 | 27 | 25 |
| 7 | 33.4 | 25.7 | 16 |
| 7.5 | 28.3 | 27.8 | 7.1 |
| 8 | 26.9 | 26.6 | 1.3 |
| 8.5 | 25.6 | 29.3 | −0.7 |
| 9 | 24.5 | 28.8 | −2.3 |
| 9.5 | 23.9 | 29.5 | −3.8 |

Figure 8A:
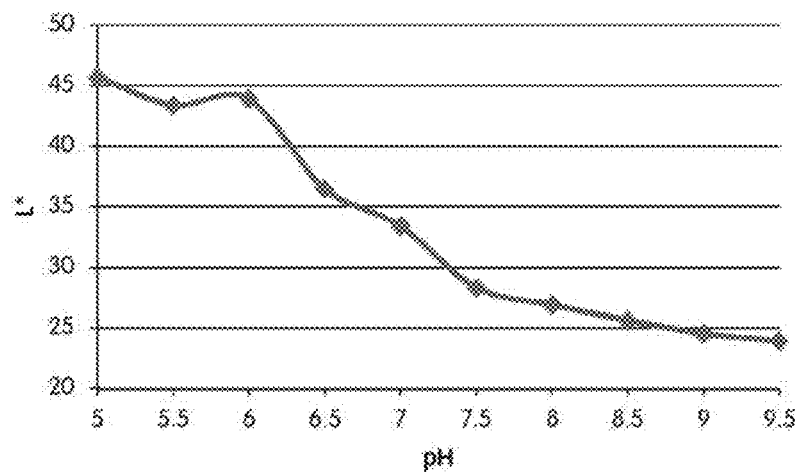
FIGS. 8A-E are graphic representations of the colour pen measurements for the Post-Op sample illustrated in FIG. 7.
Figure 8B:
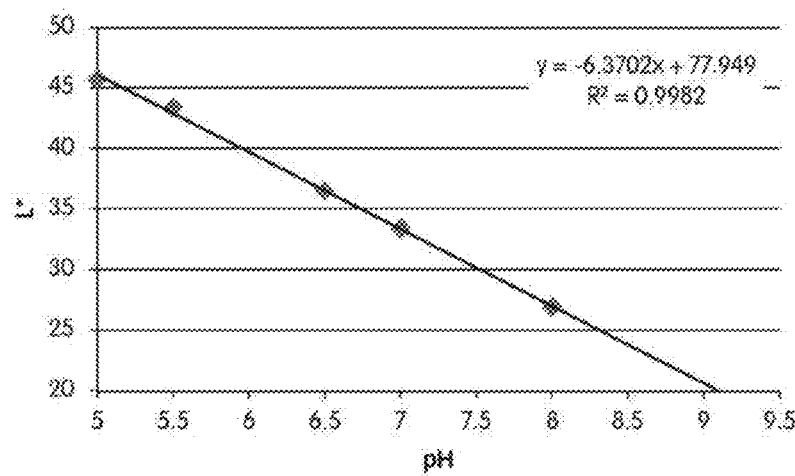

FIGS. 8A and 8B illustrate a graphical representation of the L* measurements taken with the colour pen. FIG. 8A shows all data points whilst FIG. 8B is a re-plot of the data points in the linear region between pH 5 to pH 8. The trend line has a gradient of −6.3702 with an $R^2$ value of 0.9982.

Figure 8C:
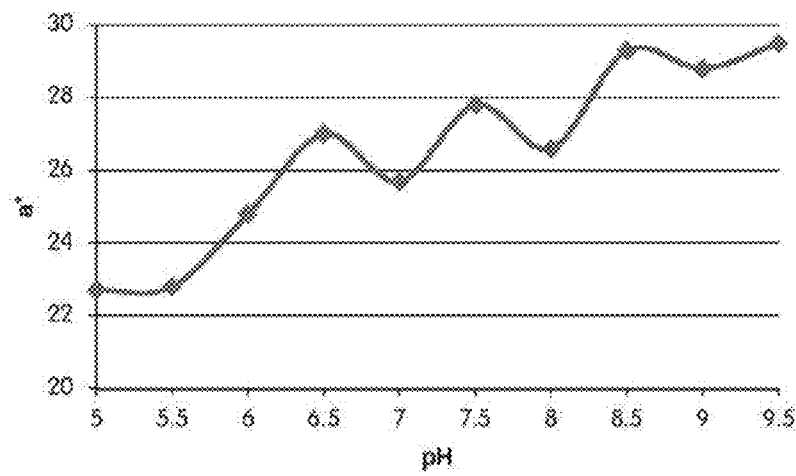

FIG. 8C illustrate the a* measurements taken with the colour pen presented graphically over the pH 5-pH 9.5 range. The results are too variable for the a* measurement to be considered of use in reliably measuring a colour change in the GJM 514:546 dye combination in response to changes in pH.

Figure 8D:
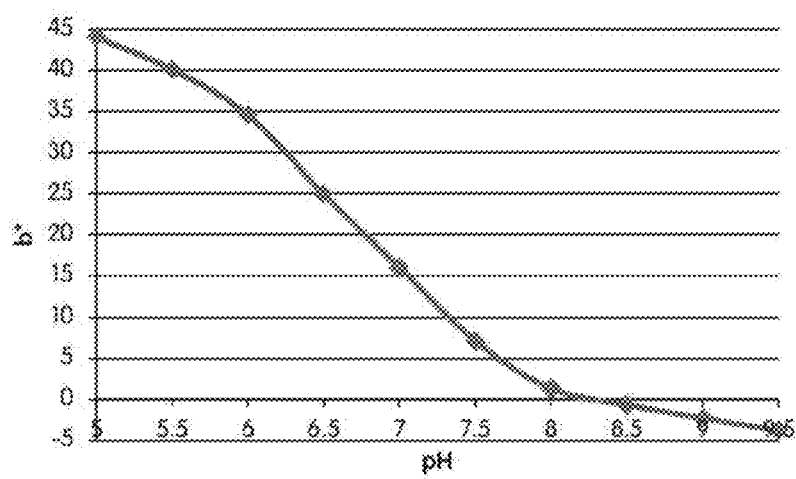
Figure 8E:
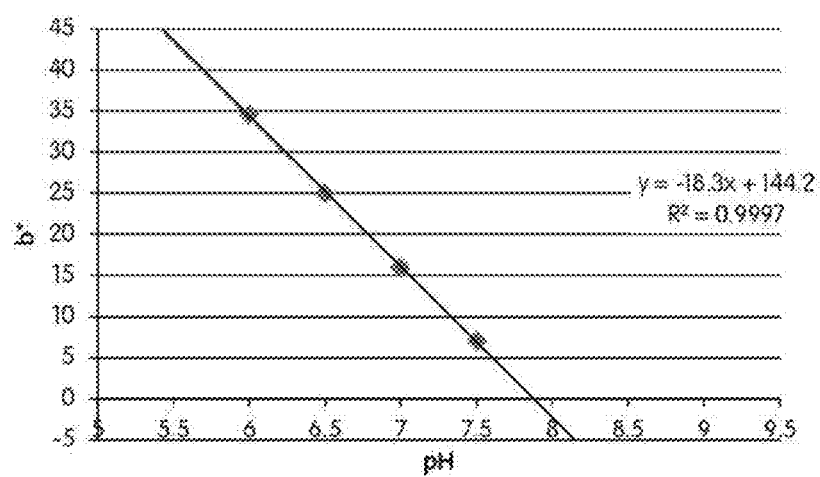

FIGS. 8D and 8E illustrate a graphical representation of the b* measurements taken with the colour pen. FIG. 8E shows the b* measurements taken at various pH values between pH 5-pH 9.5 and it can be seen that the results follow a downward trend from pH 5 to pH 8, but it appears to plateau after pH 8. FIG. 8E illustrates the b* measurements at various pH values over the linear portion of a trend line which has a gradient of −18.3 and an $R^2$ of 0.9997. As the b* results gave a steeper gradient it is believed that monitoring the b* value would give a more accurate reading of the pH from the dressing colour. The working range for this dye combination appears to be pH 6 to pH 7.5.

Example 4: Post-Op Pad Dyed with GJM 514:534 (1:1)

Figure 9:
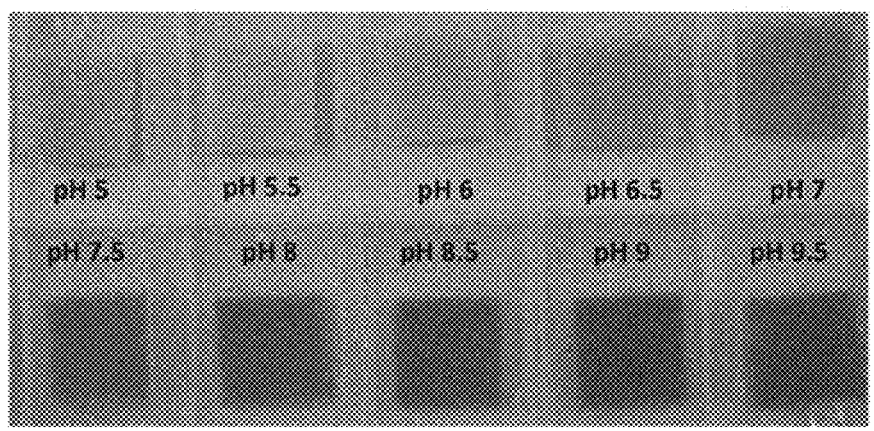
FIG. 9 is a photograph of a Post-Op sample dyed with a third combination of dyes, illustrating changes in colour of the dye combination in response to a buffered solution changing pH along a pH unit interval scale.

A sample of the pad from an Opsite. Post-Op dressing (Smith & Nephew) was covalently bound with the dye GJM 514:534 at a 1:1 ratio was exposed to buffered solutions at pH 5-pH 9.5. The panel of photographs in FIG. 9 demonstrates the colour change over this pH range, going from yellow in colour (at pH 5) to red in colour (at pH 9.5).

Table 5 illustrates the colour pen measurements (L*, a* and b*) of the colour of the GJM-514:GJM-534 dye combination over a pH range of pH 5-pH 9.5

TABLE 5

| pH | L* | a* | b* |
|---|---|---|---|
| 5 | 53.4 | 6.1 | 50.3 |
| 5.5 | 52.3 | 7.5 | 45.4 |
| 6 | 53.8 | 7.6 | 46.1 |
| 6.5 | 49.7 | 9.8 | 35.4 |
| 7 | 43.1 | 16.2 | 29.9 |
| 7.5 | 37.4 | 16.2 | 18.9 |
| 8 | 33.4 | 20.4 | 11.9 |
| 8.5 | 31.9 | 22.8 | 5.3 |
| 9 | 27.7 | 27.6 | 3.6 |
| 9.5 | 28.9 | 29.1 | −0.5 |

Figure 10A:
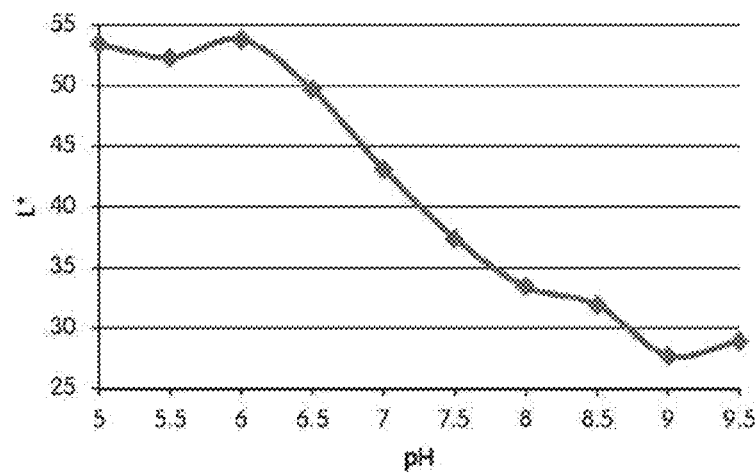
FIGS. 10A-F are graphic representations of the colour pen measurements for the Post-Op sample illustrated in FIG. 9.
Figure 10B:
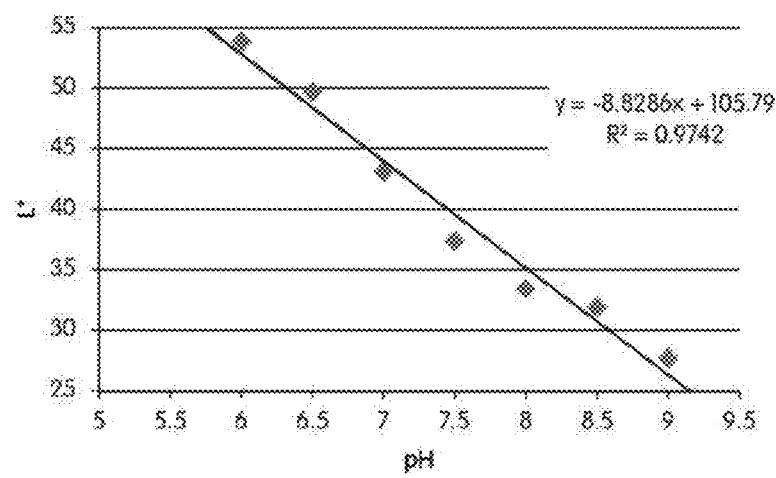

FIGS. 10A and 10B illustrate a graphical representation of the L* measurements taken with the colour pen. FIG. 10A shows all data points whilst FIG. 10B shows only those data points in the linear region. A general downward trend from pH 6 to pH 9 is observed. The trend line has a gradient of −8.8286 and an $R^2$ value of 0.9742.

Figure 10C:
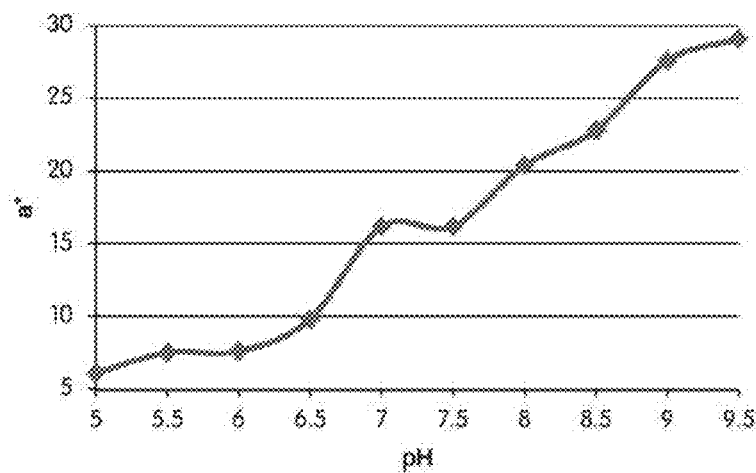
Figure 10D:
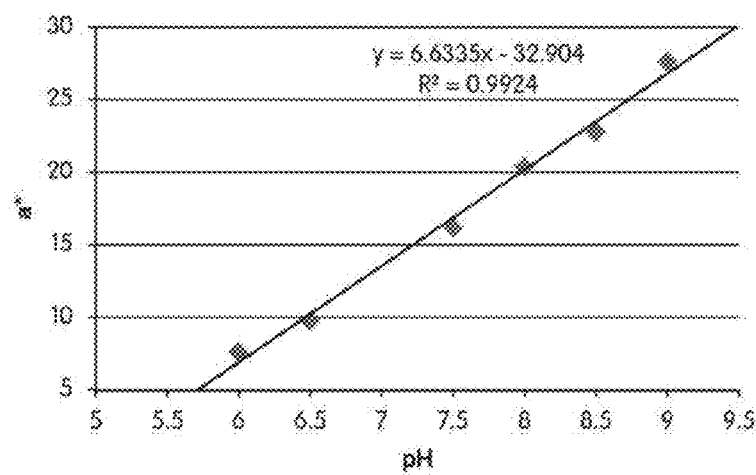

FIGS. 10C and 10D illustrate the a* measurements taken with the colour pen presented graphically. FIG. 10C illustrates the a* measurements taken at various pH values between pH 5-pH 9.5. FIG. 10D illustrates the a* measurements at various pH values over the linear portion of a trend line. The results demonstrate an upwards trend between pH 6 to pH 9, with the trend line having a gradient of 6.6335 and an $R^2$ value of 0.9924.

Figure 10E:
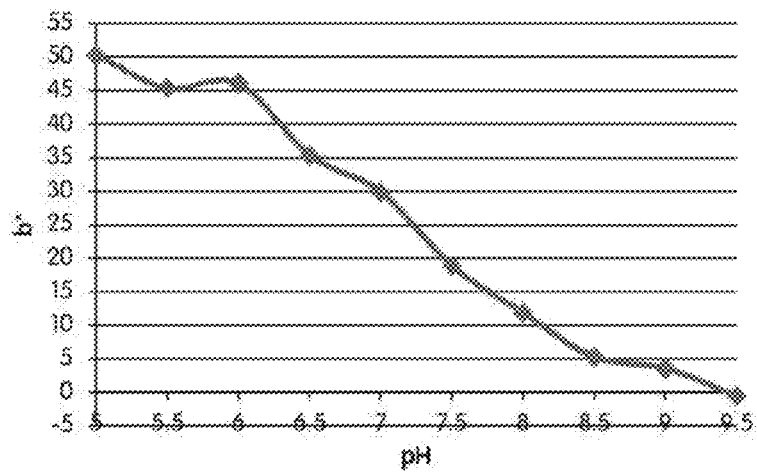
Figure 10F:
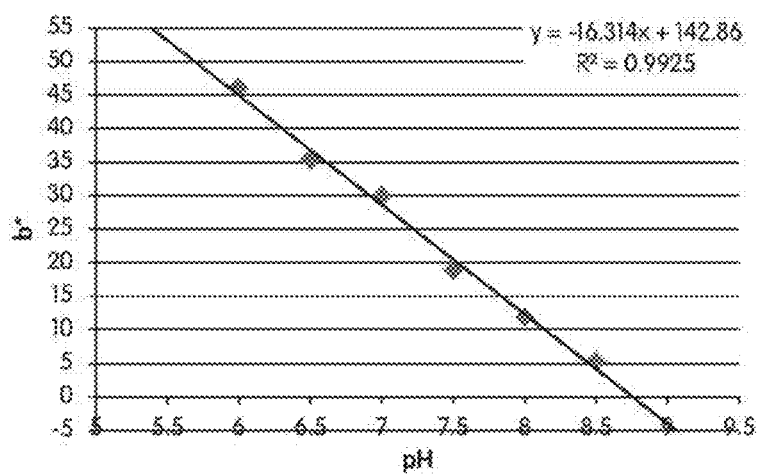

FIGS. 10E and 10F illustrate a graphical representation of the b* measurements taken with the colour pen. FIG. 10E shows the b* measurements taken at various pH values between pH 5-pH 9.5 and it can be seen that the results follow a downward trend until pH 9. The trend line illustrated in FIG. 10F has a gradient −16.314 and an $R^2$ value of 0.9925 between pH 6 and pH9. From the colour pen measurements the working range of this dye combination is between pH 6 and pH 9, and the b* value could be used to accurately measure the pH from the material colour.

Example 5: Post-Op Pad Dyed with GJM 514:534 (1:0.509)

Figure 11:
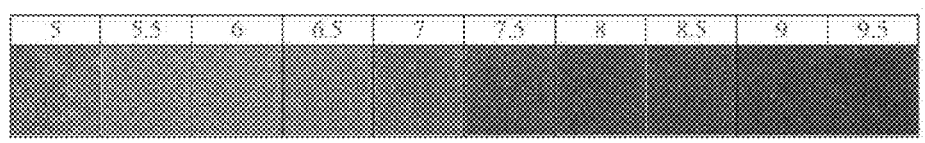
FIG. 11 is a photograph of a Post-Op sample dyed with a fourth combination of dyes, illustrating changes in colour of the dye combination in response to a buffered solution changing pH along a pH unit interval scale.

A sample of the pad from an Opsite Post-Op dressing (Smith & Nephew) was covalently bound with the dye GM 514:534 at a 1:0.509 ratio was exposed to buffered solutions at pH 5-pH 9.5. The panel of photographs in FIG. 11 demonstrates the colour change over this pH range, going from yellow in colour (at pH 5) to red in colour (at pH 9.5).

Table 6 illustrates the colour pen measurements (L*, a* and b*) of the colour of the GJM-514:GJM-534 dye combination over a pH range of pH 5-pH 9.5

TABLE 6

| pH | L* | a* | b* |
|---|---|---|---|
| 5 | 55.4 | 4.9 | 43.1 |
| 5.5 | 57.6 | 2.9 | 42.6 |
| 6 | 56.8 | 3.4 | 42.7 |
| 6.5 | 51.2 | 5 | 40 |
| 7 | 49 | 8.8 | 34.7 |
| 7.5 | 39.8 | 11.4 | 23.5 |
| 8 | 39 | 17.6 | 15 |
| 8.5 | 36.5 | 22.4 | 10.1 |
| 9 | 34.2 | 24.3 | 5.8 |
| 9.5 | 32.3 | 25.3 | 0.3 |

Figure 12A:
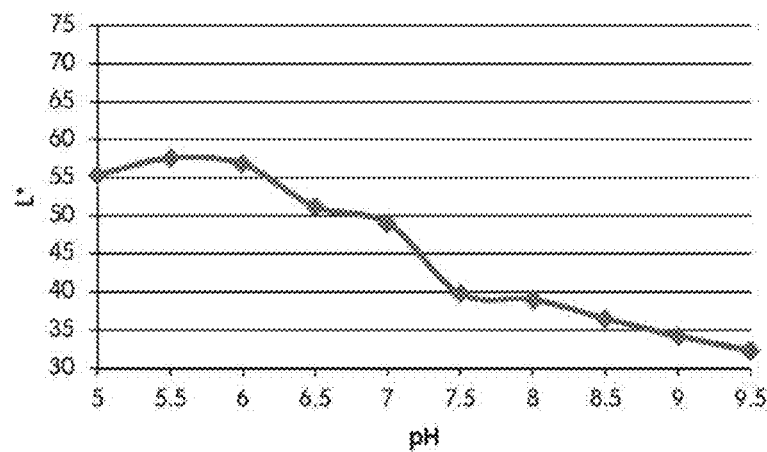
FIGS. 12A-E are graphic representations of the colour pen measurements for the Post-Op sample illustrated in FIG. 11.

FIG. 12A illustrates a graphical representation of the L* measurements taken with the colour pen. A general downward trend from pH 6 to pH 9.5 is observed.

Figure 12B:
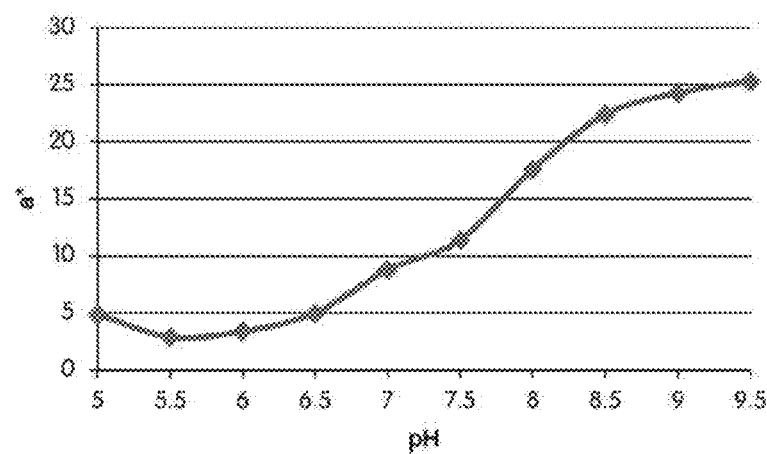
Figure 12C:
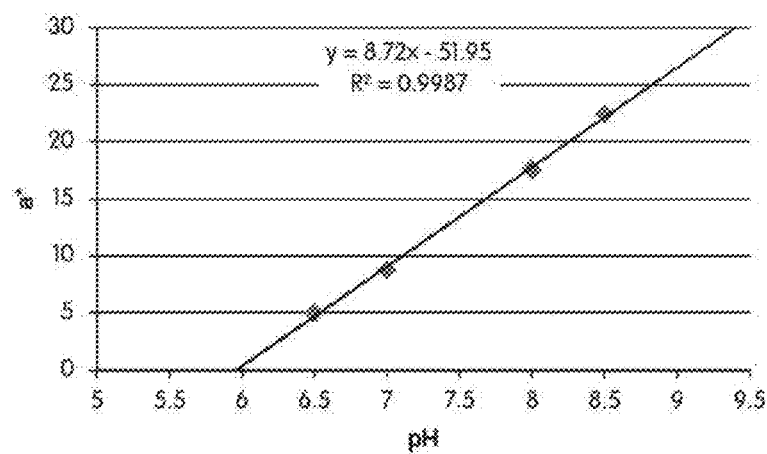

FIGS. 12B and 12C illustrate the a* measurements taken with the colour pen presented graphically. FIG. 12B illustrates the a* measurements taken at various pH values between pH 5-pH 9.5. FIG. 12C illustrates the a* measurements at various pH values over the linear portion of a trend line. The results demonstrate a linear upwards trend between pH 6.5 to pH 8.5, with the trend line having a gradient of 8.72 and an $R^2$ value of 0.9987.

Figure 12D:
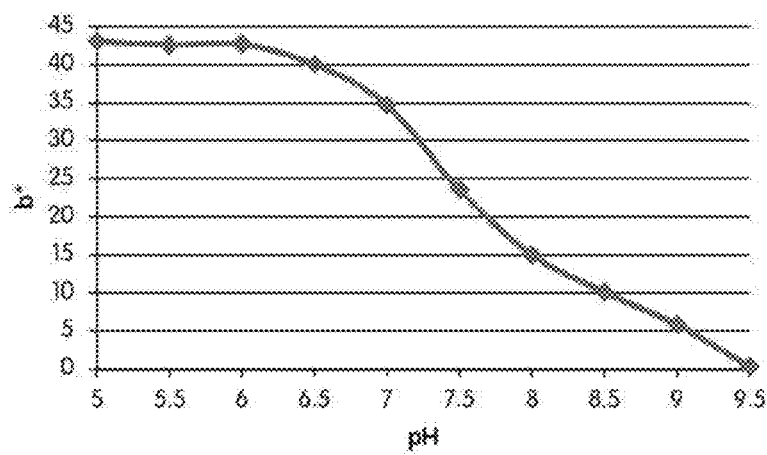
Figure 12E:
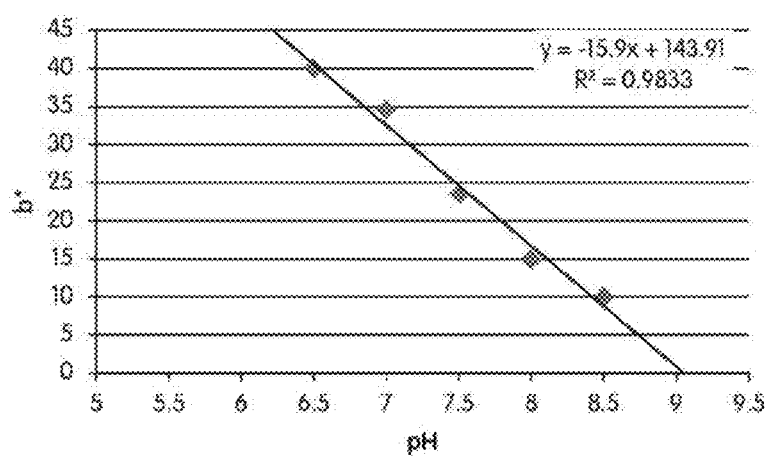

FIGS. 12D and 12E illustrate a graphical representation of the b* measurements taken with the colour pen. FIG. 12D shows the b* measurements taken at various pH values between pH 5-pH 9.5 and it can be seen that the results follow a downward trend between pH 6 and pH 8.5. The trend line illustrated in FIG. 12E has a gradient 15.9 and an $R^2$ value of 0.9833. Taking into account the colour pen results and the photographs of the samples, the working range of this dye combination is between pH 6 and pH 8.5, and the b* value could be used to accurately measure the pH from the material colour.

Examples 6 and 7

Further to the above general method for preparing covalently bonded dye, different materials were also used unto which to bind the dye.

A sample of a gauze (Kerlix Trademark of Covidiene) and polyvinyl alcohol foam (V.A.C. WhiteFoam, trade mark of KCl) were covalently bound with the dye GJM-546 and 492 in a ratio 1:3.92 as described throughout this disclosure.

These latter materials can be used as pH sensing fillers for Negative Pressure Wound Therapy (NPWT). They were evaluated by use of the following models and experiments.

Materials

| Material |
|---|
| Pork Meat (loin or shoulder 2 kg approx. Intact skin and a surface area 20 × 20 cm approx.) |
| pH sensitive VAC foam |
| pH sensitive gauze |
| Renasys drapes |
| Horse serum |
| Citric Acid |
| Sodium Bicarbonate |

Equipment

| Equipment |
|---|
| Renasys EZ plus pump |
| Peristaltic pump |
| Renasys EZ canister |
| Epidural needle |
| Clingfilm |
| Tubing |
| Glass Dish |
| Scalpel |
| pH meter |

Method

Use these solutions to adjust horse serum to pH 5 and pH 8, for use in the meat mode.
1. Place a sheet of cling film in the bottom of a glass dish/tray and place a piece of pork with intact skin upwards on the cling film.
2. Wrap the meat in the cling film and add more if necessary so that the meat is completely sealed.
3. Using a scalpel create 2 wounds each approximately 50 mm in diameter and 25 mm deep in the tissue (and at least 2 cm apart), by removing the skin/fat/muscle, with a relatively flat bottom and minimal tissue flaps.
4. Insert an epidural catheter needle through the side of the wound so that the tip appears at the outside edge of the meat. Use the needle to feed the peristaltic pump tubing through so that it lies at the base of the wound. (Repeat for the other wound).
5. Using small pieces of Flexi-fix and/or adhesive putty ("white-tac") secure and seal the openings where the fluid tubes exit the cling film.
6. The following combinations are to be tested:
   a. Dyed VAC foam
   b. Dyed gauze
7. Add foam to bridge onto intact healthy skin and link both bridges together to work from a single port. Seal over the wounds, fillers and bridging foam with drapes.
8. Make a small hole in the drape where it lies over a foam bridge and attach a port using Flexi-fix strips.
9. Connect the port to a RENASYS NPWT pump (set at −120 mmHg) and switch on.
10. Turn on the peristaltic pump (set to deliver 40 µl/min) to deliver fluid to the wound bed of horse serum at pH 8
11. Monitor the dressings until fluid starts to appear in the canister (make a note of the length of time)
12. Change the fluid to horse serum at a pH of 5, and leave to flow for the amount of time determined in step 11). Then take a photograph of the dressings.
13. Change the fluid to horse serum at a pH of 8, and leave to flow for the amount of time determined in step 11). Then take a photograph of the dressings.
14. Change the fluid back to horse serum at a pH of 5, and leave to flow for the amount of time determined in step 11). Then take a photograph of the dressings.

15. At the end of the experiment disconnect the tubing and seal the meat in cling film for disposal. Clean all surfaces that had contact with the meat with soap/water.

Determination of the ability of dyed VAC foam and gauze to detect changes in pH of wound fluid.

The pH sensitive gauze and VAC foam were washed after the first meat model experiment and then used in an additional wound model, with pH adjusted water. In addition the extra piece of pH sensitive dyed gauze was placed in a clear Perspex wound model and fluid pumped through.

All wound models were monitored by taking photographs, those carried out in meat could only be monitored from the top surface, but the clear Perspex model could be monitored from all sides.

Results and Discussion

The foam was orange in colour when it was loaded into the wound, but the gauze was more of a red colour. It is believed the gauze is red in colour due to the presence of PHMB on the gauze which would make it basic.

Meat Model 1

The experiment was started by pumping pH 5 horse serum into the wound filler for approximately 2.5 hours before fluid started to appear in the canister and the material started to change colour. After approximately 5.5 hours the pH 5 horse serum solution was changed to pH 8 horse serum and this was run overnight. In the morning the solution was then changed back to pH 5 horse serum and was pumped in for several hours (due to time restrictions the flow rate was increased to 80 μl/min after 3.5 hours).

The images of the pH sensitive dyed gauze changing over time can be seen in FIG. 13A to F; showing that the gauze had started to go orange after 5.5 hours of exposure to pH 5 horse serum and after a night of exposure to pH 8 serum the gauze had returned to a red colour. Then after several hours of exposure to pH 5 the gauze was starting to turn orange again at which time the experiment was ended. Upon removal of the gauze it could be seen that the bottom of the gauze was mostly orange and it could be seen that the colour and therefore the pH were changing through the gauze in a direction from the wound bed towards the drape, which can be explained by the fact that the wound tends to fill up like the filling of a bath and therefore the pH takes time to change from one pH to the other as the pumped fluid is slowly transported through the wound filler.

Images of the pH sensitive dyed VAC foam changing over time can be seen in FIG. 14 A to F They show that the foam had gone yellow when exposed to pH 5 horse serum (5.5 hours image), and that when exposed to pH 8 overnight the foam went red. As with the gauze the foam had started to turn yellow/orange after re-exposure to pH 5 serum for several hours before the experiment was ended, the yellow/orange colour can most clearly be seen near the bridging foam.

Meat Model 2

For the second meat model the basic aqueous solution was used first and was left pumping into the model overnight. The next morning the solution was then changed to an acidic aqueous solution and left pumping for several hours.

The images for the pH sensitive gauze can be seen in FIG. 15A to F and show that the gauze went red in colour in basic solution and within 5 hours of the fluid being switched to acidic aqueous solution the gauze had started to turn orange. It is believed that this colour change will originate at the base of the wound and work its way up to the surface as the pH in the wound changes, which as mentioned earlier would be similar to the way in which a bath fills up. It is clear the colour change on the surface starts near the area directly below the port, this can be explained as this is the destination (exit point) of the fluid and so the pH would stabilises around this area on the surface first.

The same trend is seen with the dyed VAC foam, as shown in FIG. 16A to F The foam turns red when in the presence of basic fluid and when the fluid is changed to acidic the foam starts to turn yellow in colour. Like the gauze the colour change seen on the surface is first noticeable around the port where the fluid is removed from the wound.

Clear Perspex Wound Model

The experiment was also carried out using the pH sensitive dyed gauze in a clear Perspex wound model to be able to visualise the colour change throughout the wound. The fluid was not pumped in from the bottom on this occasion but from the left hand side of the wound as seen on the images in FIG. 17A to H. The fluid inlet is on the same side as the port and halfway up the wound wall. It is believed that the area of this wound is smaller than those created in the meat, hence the colour change occurring faster as the pump speed is the same in both experiments. It can be seen that as the basic fluid is pumped into the wound the gauze turns red (at T=0 hours there was already some basic fluid in the wound hence part of the gauze already being red in colour). It can be seen from all the images in FIG. 17 A to H, both the top surface of the wound (top image) and the bottom (bottom image of each pair), that the colour change moves across the wound from left to right and that the bottom of the wound is slightly ahead of the upper surface of the wound. This colour change pattern is as expected, as fluid fills up from the bottom and so the pH changes at the bottom before the top. The Perspex model is not as realistic as the meat model as the fluid and content from the meat would mean that the pH could take longer to change due to possible buffering effects.

CONCLUSIONS AND RECOMMENDATIONS

Both the pH sensitive dyed VAC foam and gauze, changed colour as they were exposed to different pH solutions. The colours for indicating the different pH's were clearly visible, and the colour could be reversed by addition of the other pH solution to the wound.

It is to be understood that the foregoing description is merely illustrative and is not to be limited to the details given. While several embodiments have been provided in the present disclosure, it should be understood that the disclosed devices and method and their components, may be embodied in many other specific forms without departing from the scope of the disclosure.

Variations and modifications will occur to those of skill in the art after reviewing this disclosure. The disclosed features may be implemented, in any combination and sub-combinations (including multiple dependent combinations and sub-combinations), with one or more other features described herein. The various features described or illustrated above, including any components thereof may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. An article of manufacture, comprising:
   a fluid-contacting surface, wherein the article of manufacture further comprises a gel positioned on the fluid-contacting surface, the gel configured to contact the fluid, the gel comprising a pH indicator comprising 2-[(4-(2-hydroxyethylsulfonyl)-phenyl)diazenyl]-4-methylphenol and 4-[4-(2-hydroxyethylsulphonyl)-phenylazo]-2,6-dimethoxy phenol in about a 2:1 ratio.

2. The article of claim 1, wherein the gel is an adhesive.

3. The article of claim 1, further comprising a conduit configured to direct fluid to the pH indicator.

4. The article of claim 1, wherein the fluid contacting surface comprises a film.

5. The article of claim 1, wherein the fluid contacting surface comprises an absorbent pad.

6. The article of claim 1, wherein the fluid contacting surface comprises a mesh.

7. The article of claim 1, wherein the article is configured to indicate food spoilage.

8. The article of claim 7, wherein the article is configured to be positioned on a food package.

9. The article of claim 1, wherein the article is configured to be placed in a wound.

10. The article of claim 1, wherein the fluid-contacting surface is a coating, the coating configured to be placed on a packaging material.

11. The article of claim 1, wherein the article is configured to monitor drug release.

12. The article according to claim 1, wherein the colour change in the pH indicator is detectable at a 0.1 unit interval change in pH.

13. The article according to claim 12, wherein the colour change in the pH indicator is detectable between about pH 5 and about pH 10.

14. The article according to claim 13, wherein the colour change in the pH indicator is detectable between about pH 5.5 and about pH 9.5.

15. The article according to claim 13, wherein the colour change in the pH indicator is detectable between about pH 6.5 and 9.5.

16. The article according to claim 1, wherein the article comprises a cellulosic material.

17. The article according to claim 1, wherein the article comprises a peripheral edge, the pH indicator positioned on the peripheral edge.

* * * * *

UNITED STATES PATENT AND TRADEMARK OFFICE
CERTIFICATE OF CORRECTION

PATENT NO. : 10,288,590 B2
APPLICATION NO. : 15/804748
DATED : May 14, 2019
INVENTOR(S) : Victoria Jody Hammond et al.

It is certified that error appears in the above-identified patent and that said Letters Patent is hereby corrected as shown below:

In the Specification

Column 2, Line 33 (approx.), change "napthalene" to --naphthalene--.

Column 2, Line 37 (approx.), change "2,,6" to --2,6--.

Column 5, Line 65, change "KCT)" to --KCI)--.

Column 6, Line 6, change "scrum" to --serum--.

Column 6, Line 10, change "FIG." to --FIGS.--.

Column 6, Line 25, change "FIG." to --FIGS.--.

Column 6, Line 40, change "FIG." to --FIGS.--.

Column 7, Line 45, change "napthalene" to --naphthalene--.

Column 9, Line 28 (approx.), change "Pcn)," to --Pen),--.

Column 12, Line 22, change "Opsite." to --Opsite--.

Column 12, Line 30 (approx.), change "9.5" to --9.5.--.

Column 13, Line 9 (approx.), change "GM" to --GJM--.

Column 13, Line 16, change "9.5" to --9.5.--.

Column 13, Line 61, change "Covidiene)" to --Covidien)--.

Signed and Sealed this
Twenty-seventh Day of August, 2019

Andrei Iancu
*Director of the United States Patent and Trademark Office*

CERTIFICATE OF CORRECTION (continued)
U.S. Pat. No. 10,288,590 B2

Column 13, Line 63, change "KCl)" to --KCl)--.

Column 14, Line 56 (approx.), change "pH 8" to --pH 8.--.

Column 14, Line 58 (approx.), change "time)" to --time).--.

Column 15, Line 31, change "FIG." to --FIGS.--.

Column 15, Line 46, change "FIG." to --FIGS.--.

Column 15, Line 46, after "to F" insert --.--.

Column 15, Line 59, change "FIG." to --FIGS.--.

Column 16, Line 5, change "FIG." to --FIGS.--.

Column 16, Line 5, after "to F" insert --.--.

Column 16, Line 16, change "FIG." to --FIGS.--.

Column 16, Line 24, change "FIG." to --FIGS.--.

Column 16, Line 56, change "thereof" to --thereof,--.